(12) United States Patent
Knauf et al.

(10) Patent No.: US 10,577,311 B2
(45) Date of Patent: Mar. 3, 2020

(54) METHOD FOR PRODUCING ISOCYANATES

(71) Applicant: Covestro Deutschland AG, Leverkusen (DE)

(72) Inventors: Thomas Knauf, Dormagen (DE); Dirk Manzel, Moers (DE); Peter Plathen, Krefeld (DE); Jürgen Spriewald, Kölln-Reisiek (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/762,224

(22) PCT Filed: Sep. 20, 2016

(86) PCT No.: PCT/EP2016/072327
§ 371 (c)(1),
(2) Date: Mar. 22, 2018

(87) PCT Pub. No.: WO2017/050776
PCT Pub. Date: Mar. 30, 2017

(65) Prior Publication Data
US 2018/0290968 A1 Oct. 11, 2018

(30) Foreign Application Priority Data
Sep. 24, 2015 (EP) .................................... 15186734

(51) Int. Cl.
*C07C 263/10* (2006.01)
*B01J 19/24* (2006.01)

(52) U.S. Cl.
CPC ............. *C07C 263/10* (2013.01); *B01J 19/24* (2013.01); *B01J 2219/00222* (2013.01); *B01J 2219/00225* (2013.01); *B01J 2219/24* (2013.01)

(58) Field of Classification Search
None
See application file for complete search history.

(56) References Cited

U.S. PATENT DOCUMENTS

| | | |
|---|---|---|
| 4,764,308 A | 8/1988 | Sauer et al. |
| 4,851,570 A | 7/1989 | Zaby et al. |
| 5,136,087 A | 8/1992 | Van Horn et al. |

(Continued)

FOREIGN PATENT DOCUMENTS

WO    2013029918 A1    3/2013

OTHER PUBLICATIONS

W. Siefken, Liebigs Ann. 562, 75-106 (1949).
(Continued)

*Primary Examiner* — Jennifer A Leung
(74) *Attorney, Agent, or Firm* — N. Denise Brown

(57) ABSTRACT

The invention relates to a method for an economically and technically improved embodiment of a production interruption in a production method for isocyanates by phosgenation of the corresponding amines, in which the entire production plant is not closed while one or more parts of the plant is taken out of operation, rather the input materials and/or reaction products available in the production plant are recirculated through at least one part of the plant that has not been taken out of operation. The invention further relates to a plant for producing isocyanates and to a method for operating a plant for producing isocyanates.

17 Claims, 5 Drawing Sheets

(56) References Cited

U.S. PATENT DOCUMENTS

| | | | |
|---|---|---|---|
| 5,599,968 | A | 2/1997 | Bankwitz et al. |
| 7,038,002 | B2 | 5/2006 | Pirkl et al. |
| 7,118,653 | B2 | 10/2006 | Brady et al. |
| 7,414,149 | B2 * | 8/2008 | DeCourcy ............... B01J 19/002 562/532 |
| 7,442,835 | B2 | 10/2008 | Keggenhoff et al. |
| 7,547,801 | B2 | 6/2009 | Pohl et al. |
| 7,584,629 | B2 | 9/2009 | Sohn et al. |
| 7,592,479 | B2 | 9/2009 | Stroefer et al. |
| 7,645,900 | B2 | 1/2010 | Lorenz et al. |
| 8,079,752 | B2 | 12/2011 | Rausch et al. |
| 8,097,751 | B2 | 1/2012 | Koch et al. |
| 8,153,838 | B2 | 4/2012 | Bulan et al. |
| 8,288,584 | B2 | 10/2012 | Knoesche et al. |
| 8,759,569 | B2 * | 6/2014 | Schelling ............... C07C 263/10 560/347 |
| 10,023,524 | B2 * | 7/2018 | Knauf ................... B01J 19/2465 |
| 2006/0011463 | A1 * | 1/2006 | Sohn ..................... C07C 263/20 203/29 |
| 2006/0223966 | A1 * | 10/2006 | Brodhagen ............ B01J 19/242 528/44 |
| 2007/0261437 | A1 | 11/2007 | Boonstra et al. |
| 2008/0147208 | A1 * | 6/2008 | Mahrenholtz ........ B01J 19/0033 700/28 |
| 2010/0298596 | A1 | 11/2010 | Keggenhoff et al. |
| 2012/0095255 | A1 * | 4/2012 | Mattke .................. C07C 263/10 560/347 |
| 2012/0123152 | A1 * | 5/2012 | Bruns ................... C07C 263/10 560/347 |

OTHER PUBLICATIONS

Ullmanns Encyklopädie der technischen Chemie [Ullmann's Encyclopedia of Industrial Chemistry], 4th ed. (1977), vol. 13, p. 351 to 353.

G. Wegener et. al. Applied Catalysis A: General 221 (2001), p. 303-335, Elsevier Science B.V.

Ullmann's Encyclopedia of Industrial Chemistry, 5th ed. vol. A 19, p. 413ff., VCH Verlagsgesellschaft mbH, Weinheim, 1991.

Mitchell et al.: Selection of carbon catalysts for the industrial manufacture of phosgene; Catal. Sci. Technol., 2012, 2, 2109-2115.

* cited by examiner

METHOD FOR PRODUCING ISOCYANATES

CROSS-REFERENCE TO RELATED APPLICATIONS

This application is a national stage application under 35 U.S.C. § 371 of PCT/EP2016/072327, filed Sep. 20, 2016, which claims the benefit of European Application No. 15186734.8, filed Sep. 24, 2015, both of which are being incorporated by reference herein.

FIELD

The invention relates to a process for improved configuration, from an economic and technical point of view, of a production shutdown in a preparation process for isocyanates by phosgenation of the corresponding amines, in which, during the shutdown of one or more plant sections, not the entire production plant is stopped, and instead feedstocks and/or reaction products present in the production plant are guided through at least some of the plant sections that have not been shut down in circulation mode. The present invention further relates to a plant for preparation of isocyanates and to a process for operating a plant for preparation of isocyanates.

BACKGROUND

The industrial scale preparation of di- and polyisocyanates by reaction of the corresponding amines with phosgene has long been known from the prior art, and the reaction can be conducted in the gas or liquid phase and batchwise or continuously (W. Siefken, Liebigs Ann. 562, 75-106 (1949)). Processes for preparing organic isocyanates from primary amines and phosgene have already been described many times before; see, for example, Ullmanns Encyklopadie der technischen Chemie [Ullmann's Encyclopedia of Industrial Chemistry], 4th ed. (1977), volume 13, p. 351 to 353 and G. Wegener et. al. Applied Catalysis A: General 221 (2001), p. 303-335, Elsevier Science B.V. There is use here on the global scale both of aromatic isocyanates, for example methylene diphenyl diisocyanate (MMDI—"monomeric MDI"), polymethylene polyphenylene polyisocyanates (i.e. the higher homologs of MMDI, including PMDI, "polymeric MDI"; these are always obtained in industry in a mixture with MMDI components) or tolylene diisocyanate (TDI), and of aliphatic isocyanates, for example hexamethylene diisocyanate (HDI) or isophorone diisocyanate (IPDI).

The industrial scale preparation of phosgene which is used in the phosgenation of the corresponding amines from CO and chlorine over activated carbon catalysts in a shell and tube reactor is likewise known from the prior art (e.g. Ullmann's Encyclopedia of Industrial Chemistry, 5th ed. Vol. A 19, p. 413ff., VCH Verlagsgesellschaft mbH, Weinheim, 1991). This involves combining carbon dioxide in a stoichiometric excess with chlorine and passing them over a fixed bed catalyst. The catalyst used for industrial purposes is activated carbon, and the selection of a suitable activated carbon is made empirically to the present day (Mitchell et al.: Selection of carbon catalysts for the industrial manufacture of phosgene; Catal. Sci. Technol., 2012, 2, 2109-2115).

WO 2009/037179 A1 is concerned with a process for preparing isocyanates with minimum stockpiling of phosgene and a minimum amount of phosgene present in each of the process stages. For this purpose, the application proposes a process in which the phosgene present in the process stages is essentially in gaseous form.

WO 2013/029918 A1 describes a process for preparing isocyanates by reacting the corresponding amines with phosgene, which can also be conducted at different plant loads without any problems; more particularly, even in the case of operation of the plant within the partial load range, the mixing and/or reaction is to be effected within the dwell time window optimized in each case, by increasing the ratio of amine to phosgene or adding one or more inert substances to the phosgene and/or amine stream. The process of the invention is said to enable operation of an existing plant at different modes with uniform product and process quality. This is intended to dispense with the procurement of multiple plants with different nameplate capacities.

The application teaches that essential parameters of a phosgenation such as, in particular, the residence times of the coreactants in the individual apparatuses are optimized for the operation of the production plant at nameplate capacity, which can lead to problems with regard to yield and product purity when the plant is run at lower than nameplate capacity (cf. page 2 lines 20 to 36). In order to be able to attain the optimized—narrow—dwell time window even at partial load (i.e. compared to operation at nameplate capacity with reduced amine flow), it is suggested that either the phosgene flow and/or the level of inerts be increased (cf. page 3 lines 5 to 19), preferably in such a way that the total flow rate of all components corresponds essentially to that at nameplate capacity (cf. page 6 lines 4 to 8). The application does mention startup and shutdown processes in the description of the background of the invention claimed on page 2, but does not disclose any technical teaching at all with regard to the specific procedure by which a production plant not in operation (i.e. with the amine flow and hence the flow of isocyanate produced equal to zero) is most advantageously brought to the desired operating state of nameplate capacity, or by which a production plant in operation is most advantageously shut down (i.e. the amine flow is reduced to zero, such that no further isocyanate can be produced). The technical measures disclosed in the application (i.e. the increase in the phosgene flow and/or the level of inerts) are to be viewed exclusively in the context of the problem of operation (i.e. the amine flow is significantly greater than zero) of a production plant at lower than nameplate capacity, or of the problem of how a plant being operated at nameplate capacity can advantageously be switched to operation at lower than nameplate capacity (see the examples).

The reaction output from the phosgenation line can, as described in EP 1 546 091 B1, be worked up. The reaction product is worked up in a laminar evaporator, preferably a falling-film evaporator, in which phosgene and HCl are gently evaporated.

U.S. Pat. No. 5,136,087 (B) likewise describes the removal of phosgene from the reaction mixture from the phosgenation by means of an inert solvent vapor that can originate from the solvent recovery of the phosgenation plant.

One possible embodiment of the solvent removal and recovery is described in EP 1 854 783 B1. Di- and polyisocyanates from the diphenylmethane series (MDI) which have been obtained by reaction of appropriate amines dissolved in a solvent with phosgene are first freed of hydrogen chloride and excess phosgene, and then a distillative separation of this crude solution into isocyanates and solvents is conducted. The solvent is recycled into the process for preparation of solutions of the feedstocks for the polyisocyanate preparation.

The quality of a process for preparing di- and polyisocyanates is defined firstly by the content of unwanted secondary components and impurities in the crude product that arise from improper running of the reaction. Secondly, the quality of a process is defined in that the overall process can be operated without technical production outage or problems that necessitate intervention into the process, and that losses of feedstocks can be avoided or at least minimized.

Such problems can arise on startup (putting the production plant into operation) or shutdown (stopping the production plant) for the phosgenation of the corresponding amines Problems of this kind may, for example, be that solids are formed, which lead to caking and blockage in the equipment (mixer, nozzle, reactor walls, conduits, etc.). A further disadvantage is that, in the event that inspection, maintenance, repair and cleaning operations are necessary on or in a reactor or another plant section, it is regularly necessary always to switch off all plant sections since the process steps build on one another and hence always proceed successively. As a result, the entire plant has to be emptied, which results in a considerable amount of reject material and is very time-consuming. Furthermore, energy has to be expended in order to bring reactors and plant sections back to the respective operating temperatures. Such production shutdowns for plant inspections, repair and cleaning measures or shortfalls of raw material or auxiliary that occur, whether planned or unplanned, are recurrent plant states which have a considerable influence on the economic operation of a plant or process that works continuously.

Although the prior art processes described are successful in preparing di- and polyisocyanates with high yield without resulting in a loss of quality in the end products, the only processes described are in the normal state of operation. Production stoppages for plant inspections, repair and cleaning measures or, for example, shortages of raw material auxiliary are not taken into account. At the same time, production shutdowns, planned or unplanned, are recurrent plant states which have a considerable influence on the economic operation of a continuously operating plant.

Such a production shutdown may be an inspection shutdown which is planned in advance, for which purpose the plant is run down, the energy supplies are switched off and typically all plant sections that are to be inspected are opened and cleaned for the purpose of examination. Such an inspection may take one or more weeks. After the inspection has ended, the production plant is closed, inertized if necessary, provided with auxiliaries and, once the appropriate forms of energy and raw materials are available, started up again. However, a production shutdown is not necessarily associated with opening or any other mechanical intervention into a reactor or another apparatus in the plant, but may also be connected to the shutdown and restarting of the production plant for various other reasons, as, for example, in the event of a failure in the raw material supply. In such a case, the plant is typically run in part-load operation and, in the worst case, when the logistical supply chain is interrupted, has to be shut down. Furthermore, production shutdowns may be forced by requirements for maintenance, cleaning or repair in the production plant. Shutdowns here in the preparation process for di- and polyisocyanates are typically described as short when production is stopped for up to one day. It is a feature of all these production shutdowns in practice that there are losses of production, and that, on restarting of the plant, for example when inertization is necessary, nitrogen is consumed or, in the heating of the plant or the feedstocks, forms of energy such as steam and power are required.

The person skilled in the art is aware that an industrial process operated semicontinuously or continuously proceeding from a production plant in operation cannot be switched instantaneously to a production shutdown, but has to be run down in a controlled manner beforehand. This is also the case for a plant outage in the event of an accident. In order to be able to produce again after the production shutdown, the plant has to be run back up to the process parameters prior to the production shutdown. Reactants and apparatuses have to be heated up, apparatuses may have to be inertized, and the loading of the apparatuses with the reactants is gradually increased to the desired target value. During this startup phase, there is thus still loss of production volume, and a disproportionate amount of energy has to be expended in order to prepare the cooled plant for startup and then to run it up to the desired target value with observation of all operationally relevant parameters as well.

What would thus be desirable would be a process in which simple measures enable optimization of production shutdowns in the operation of the preparation process for di- and polyisocyanates in terms of time taken, energy consumption, auxiliary and raw material consumption and/or reduction in wastes. This would lead to a not inconsiderable degree of improvement in productivity or economic viability of a continuously operated process or a corresponding production plant.

SUMMARY

It has been found that, surprisingly, this object is achieved for a preparation process for di- and polyisocyanates when (expressed in simplified form and without restriction thereto), during a brief shutdown, as many plant sections as possible are put in circulation mode, in order to be able to start up the overall plant again as quickly as possible after the measure. It has also been found that, surprisingly, the energy consumption in a plant put in circulation mode for 30 minutes up to 1 day is sometimes smaller than in the case of a complete shutdown of the plant for one day with a new startup. By means of a controlled circulation mode in the plant sections that are not affected by the brief shutdown, various advantages are implemented, as is still to be elucidated in detail further down.

The present invention therefore provides the following:

A process for preparing isocyanates (1), comprising the steps of:

I) reacting an amine (2) with phosgene (3) in the liquid phase in a reaction zone (1000) comprising I.1) a unit (1020) for providing an amine (2), preferably in the form of an amine solution (20) in a solvent (4), I.2) a unit (1030) for providing phosgene (3), preferably in the form of a phosgene solution (30) in a solvent (4), I.3) a unit (1040) for providing a solvent (4), I.4) a mixing unit (1100) for mixing amine (2) or amine solution (20) with phosgene (3) or phosgene solution (20) and optionally further solvent (4) and I.5) a reaction space (1200) arranged downstream of the mixing unit, with a separator unit (1210) optionally connected downstream, where the amine (2), preferably in the form of an amine solution (20), with a mass flow rate $m_2$ from the unit 1020 and the phosgene (3), preferably in the form of a phosgene solution (30), with a mass flow rate $m_3$ from the unit 1030 and optionally solvent (4) from the unit 1040 with a mass flow rate $m_4$ are conducted into the mixing unit 1100 and mixed therein, and the mixture obtained is converted in the downstream reaction space and separated into a liquid stream (60) comprising crude isocyanate and solvent (and traces of phosgene and hydrogen chloride), and a gaseous stream (70) comprising phosgene and hydrogen chloride (and traces of solvent);

II) separating the liquid stream (60) from step I) into a liquid stream (80) comprising solvent and crude isocyanate (and traces of phosgene), and a gaseous stream (90) comprising phosgene and hydrogen chloride (and traces of solvent) in a distillation apparatus (2100—"dephosgenation column");

III) separating the liquid stream (80) into a gaseous stream (110) comprising solvent (and traces of phosgene) and a liquid stream (100) comprising crude isocyanate (and traces of solvent) in a distillation apparatus (2200—"solvent column");

IV) separating the gaseous stream (110), preferably after it has been liquefied in a condenser (2310), into a liquid stream (120) comprising solvent and a gaseous stream (130) comprising phosgene in a distillation apparatus (2300—"solvent stripper");

V) obtaining a liquid isocyanate stream (140) from the liquid stream (100), resulting in a gaseous stream (150) comprising secondary components and optionally solvent, in a distillation apparatus (2400), optionally comprising the removal of polymeric isocyanate fractions in an upstream unit for polymer removal (2410—"polymer removal", PMA) as stream (141);

VI) absorbing the gaseous streams (70), (90) and (130) in solvent (4) to obtain a liquid stream (160) comprising solvent and phosgene, and a gaseous stream (170) comprising hydrogen chloride in an absorption apparatus (2500—"phosgene absorber");

VII) optionally and preferably, absorbing the gaseous stream (170) in water or dilute hydrochloric acid in a further absorption apparatus (2600—"HCl absorption column");

VIII) optionally and preferably, cleaning offgas streams at least from VII), preferably cleaning offgas streams from all the plant sections present, in an apparatus for offgas cleaning (3000);

IX) optionally and preferably, preparing phosgene (3) from carbon monoxide and chlorine in a phosgene generation apparatus (4000) connected to the unit (1030) for provision of phosgene;

where in a shutdown of one or more plant sections from steps (I) to (IX), insofar as they are implemented, the mass flow rate $m_2$ is reduced to zero and, in at least one of the plant sections that is not being shut down, the output stream from this at least one plant section which is not being shut down (i) is recycled into the respective plant section or (ii) is conducted into a plant section which is upstream or downstream and thence, optionally via further plant sections that have not been shut down, recycled into the original plant section (called "circulation mode"). What is brought about in this way is that a stream flows continuously through the at least one plant section which has not been shut down. The procedure is preferably followed in all plant sections that have not been shut down, meaning that preferably all plant sections that have not been shut down as per (i) or (ii) are operated in circulation mode or incorporated into a circulation mode.

The present invention further provides a plant for preparation of isocyanates in the liquid phase, as is still to be described in detail further down, and which is suitable for the performance of the process of the invention.

Finally, the present invention provides a process for operating a plant for preparation of isocyanates in the liquid phase, which is still to be described in detail further down.

DETAILED DESCRIPTION

Figure 1:
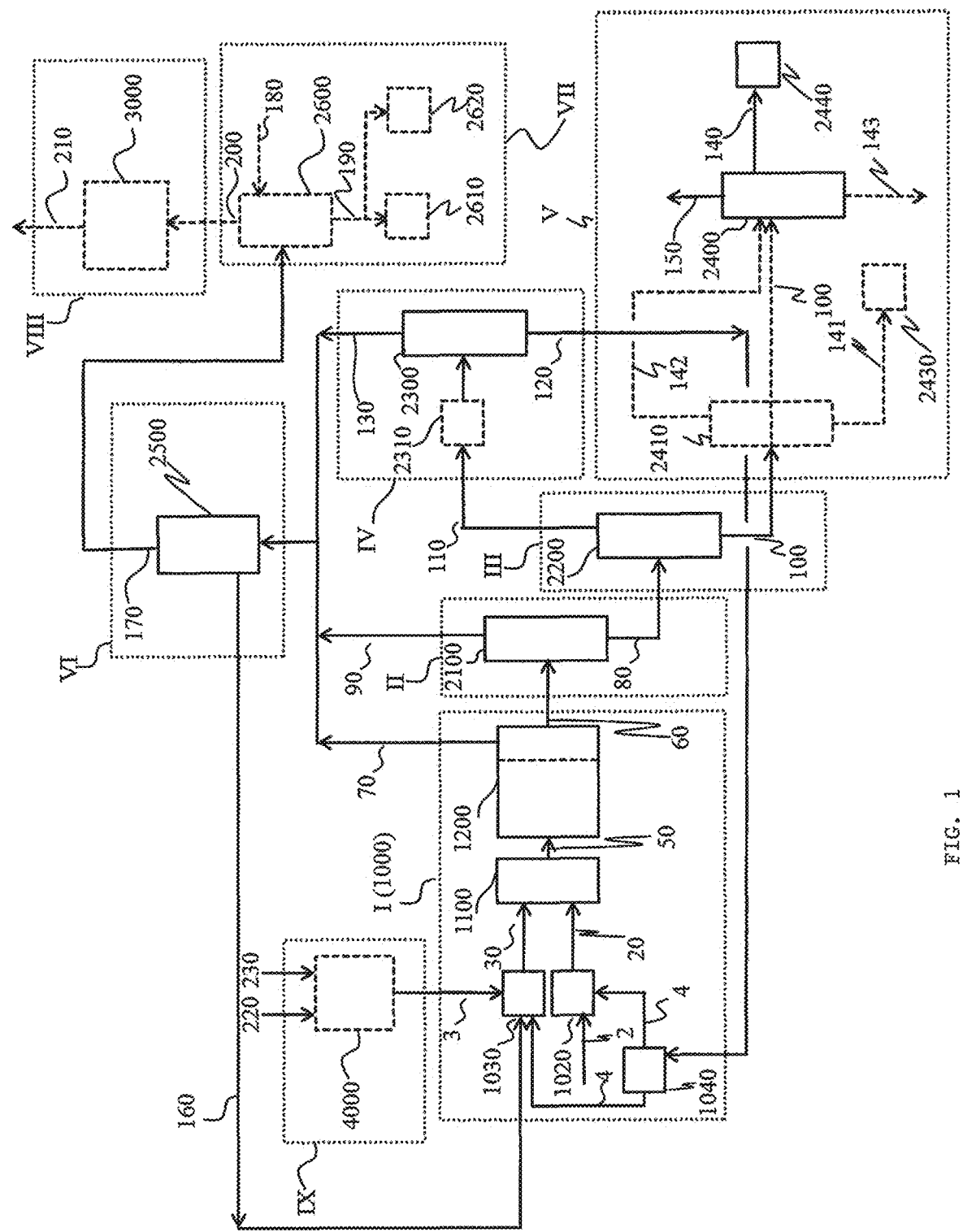
FIG. 1 illustrates the normal process flow for the preparation of isocyanates when operating the process and the plant under normal conditions.

The process of the invention is operated continuously in regular operation. This means that the plant sections from steps (I) to (IX), insofar as they are implemented, during the production, i.e. while the mass flow $m_2$ is non-zero ($m_2 \neq 0$), are charged continuously with the appropriate input streams (e g amine solution and phosgene solution into the mixing unit 1100), and the respective products (e.g. the liquid stream (60) comprising crude isocyanate and solvent (and traces of phosgene and hydrogen chloride), and the gaseous stream (70) comprising phosgene and hydrogen chloride (and traces of solvent) are withdrawn therefrom.

The process of the invention is suitable in principle for preparation of any desired aromatic, aliphatic and araliphatic isocyanates (1). Preference is given to using the process of the invention for preparation of methylene diphenyl diisocyanate (from methylenediphenyldiamine), polymethylene polyphenylene isocyanate (from polymethylenepolyphenylenepolyamine), mixtures of methylene diphenyl diisocyanate and polymethylene polyphenylene isocyanate, tolylene diisocyanate (from tolylenediamine), xylylene diisocyanate (from xylylenediamine), hexamethylene diisocyanate (from hexamethylenediamine), isophorone diisocyanate (from isophoronediamine) and naphthyl diisocyanate (from naphthyldiamine), more preferably of methylene diphenyl diisocyanate, mixtures of methylene diphenyl diisocyanate and polymethylene polyphenylene polyisocyanate, and tolylene diisocyanate. The process of the invention is most preferably suitable for preparation of methylene diphenyl diisocyanate and mixtures of methylene diphenyl diisocyanate and polymethylene polyphenylene polyisocyanate. Isocyanates (1) are obtained in the process of the invention at least in stream (140), where (140) may also cumulatively represent different isocyanate streams (1) of different isomer composition (140-1, 140-2, . . . ), if the distillation in 2400 includes not just a purification but also an isomer separation (see the detailed elucidations further down). In addition, the stream 141 obtained in particular embodiments also contains isocyanates (1), where stream 141 comprises, in particular, polymeric isocyanate fractions (i.e. isocyanates (1) that can be derived from polymerized amines, for example polyisocyanates from the diphenylmethane series having three or more benzene "nuclei"). "Residue stream" 143 which is also obtained in particular embodiments (cf. FIG. 1 and the detailed elucidations in this regard further down) also contains isocyanate, which can be obtained from this stream.

Suitable inert solvents (4) usable in accordance with the invention are solvents that are inert under the reaction conditions, for example monochlorobenzene, dichlorobenzene (especially the ortho isomer), dioxane, toluene, xylene, methylene chloride, perchloroethylene, trichlorofluoromethane or butyl acetate. The inert solvent (4) is preferably essentially free of isocyanate (target proportion by mass<100 ppm) and essentially free of phosgene (target proportion by mass<100 ppm), and this should be noted when using recycling streams. Preference is therefore given to working by a process as described in EP 1 854 783 A2. The solvents can be used individually or in the form of any desired mixtures of the solvents mentioned by way of example. Preference is given to using monochlorobenzene (MCB) or ortho-dichlorobenzene (ODB).

Suitable units 1020, 1030 and 1040 are, for example, tank vessels, wherein a unit 1020, 1030 or 1040 may in each case also comprise multiple tank vessels (for example in the form of a tank farm).

Suitable mixing units 1100 are sufficiently well known from the prior art.

The reaction space 1200 is a dwell time unit in which the mixture obtained in the mixing unit 1100 is given sufficient opportunity to react to completion. Suitable apparatuses are sufficiently well known from the prior art.

The separation of the crude process product into liquid stream 60 and the gaseous stream 70 is effected in the reaction space thereof or in a downstream separator unit 2010. It is also possible to integrate the mixing unit and the reaction space or the mixing unit, the reaction space and the separator unit or the reaction space and the separator unit in a single apparatus (for example in a corresponding reactor). According to the invention, it is also possible for multiple mixing units and/or reaction spaces and/or, if present, separating units to be connected in series or in parallel; for example in the form of a cascade of multiple series-connected reactors. (In other words, in designations used in accordance with the invention such as "a mixing unit", "a reaction space" and the like, the word "a" should be regarded as the indefinite article and not as meaning "one". The same does of course also apply to other apparatuses of other plant sections as well).

In the context of the present invention, in all embodiments, the "shutdown of one or more plant sections from steps (I) to (IX), insofar as they are implemented" is implemented. The "shutdown" of a plant section means the stoppage thereof, such that an inspection, repair, maintenance or cleaning measure can be conducted in the plant section. The present invention is thus concerned with those production shutdowns which can be described as "brief shutdowns" for inspection, repair, cleaning or maintenance purposes in sections of the plant or, for example, as a result of a time-limited lack of feedstocks or auxiliaries. The present invention makes it possible to implement such a measure in a plant section without having to shut down the entire production plant. Instead, the present invention enables continued operation of plant sections not affected by the inspection, repair, maintenance or cleaning measure, or of the corresponding process steps, in circulation mode (admittedly without formation of further isocyanate). Thus, the complete shutdown of the plant is restricted to exceptional (rare) cases, for instance that of complete plant inspection.

According to the invention, the term "shutdown" accordingly encompasses, in the case of presence of n plant sections within the meaning of the present invention (in this regard, see also the paragraph which follows), where n is a natural number, the shutdown of a maximum of n−1 of these plant sections. According to the invention, at least one plant section is thus not "shut down" (i.e. at least one plant section is not completely stopped). Preferably, the present invention is concerned with the case of shutdown of 1 to 2 plant sections, more preferably of 1 plant section. According to the invention, therefore, in the case of shutdown of a plant section (or two or more plant sections, but not all plant sections), the formation of further product is always stopped (since the mass flow rate $m_2$ is being reduced to zero and, therefore, no further isocyanate can be produced).

"Circulation mode" is understood in the context of this invention to mean that the output stream of a plant section is ultimately used again as input stream for this plant section. This can be accomplished in such a way that the output stream is recycled immediately back into the same plant section. It is also possible (and preferable) that the output stream from the preceding plant section is recycled into the preceding plant section only after passing through one or more further plant sections, in which case the further plant section(s) may be connected up- or downstream of the preceding plant section. In this context, "plant section" means the plant section corresponding to the respective step (I) to (IX), insofar as they are implemented, in a plant for preparation of isocyanate (and preferably also phosgene) by the process of the invention. If the respective step (I) to (IX) comprises multiple apparatuses, each of these apparatuses may be regarded as the plant section. A circulation mode of the invention may thus comprise, for example, the entire reaction zone 1000 or else only portions thereof. It is likewise possible that plant sections from multiple steps are encompassed by a circulation mode.

The distillation apparatus 2100 (called the "dephosgenation column"), the distillation apparatus 2200 (called the "solvent column"), the distillation apparatus 2300 (called the "solvent stripper"), the distillation apparatus 2400 and the optionally present unit 2410 (called the "polymer removal"), the absorption apparatus 2500 (called the "phosgene absorber"), the absorption apparatus 2600 (called the "HCl absorption column"), the offgas cleaning apparatus 3000 and the phosgene generation apparatus 4000 may in principle be configured and operated in regular operation as known from the prior art. From an apparatus point of view, however, it will generally be necessary in existing production plants to provide additional pipelines, valves and the like in order to be able to implement the circulation modes of the invention. These and other aspects of the invention are still to be elucidated in detail further down.

It will be appreciated that the plant sections, as well as the apparatuses detailed explicitly above, may also include peripheral equipment, for example pumps, heat exchangers and the like.

Embodiments of the invention are described hereinafter. They can be combined with one another as desired unless the opposite is apparent from the context.

The preparation of isocyanates in regular operation can be summarized by way of example as follows (cf. also FIG. 1):

a) Core operation of step I): the amine is reacted with phosgene in a solvent to give corresponding isocyanate, and the crude process product obtained is separated into a liquid stream (60) comprising the crude isocyanate and solvent (and traces of phosgene and hydrogen chloride) and a gaseous stream (70) comprising phosgene and hydrogen chloride (and traces of solvent).

b) Core operation of step II): removal of further hydrogen chloride formed in the reaction together with unconverted phosgene from stream 60 in what is called the dephosgenation column 2100, c) Core operation of step III): removal of solvent from the liquid stream 80 obtained in step II) in what is called the solvent column 2200.

d) Core operation of step IV): removal of phosgene from the gaseous stream 110 obtained in step III), preferably after liquefaction thereof in a condenser (2310), in what is called the solvent stripper 2300.

e) Core operation of step V): removal of solvent from the liquid stream 100 obtained in step III) by means of distillation (2400), optionally comprising the removal of polymeric isocyanate fractions (141), to obtain the isocyanate stream 140.

f) Core operation of step VI): absorption of the gaseous streams from steps I), II) and III) in a solvent in what is called the phosgene absorber 2500.

g) Core operation of step VII) (optional): absorption of the gas stream 170 obtained in step VI) in water or dilute hydrochloric acid in what is called the HCl absorption column 2600.

h) Core operation of step VIII) (optional): cleaning of the offgas streams from step VII), preferably the offgas streams from all steps, in an offgas cleaning apparatus 3000.

i) Core operation of step IX) (optional): preparation of phosgene from chlorine and carbon monoxide in a phosgene generation apparatus 4000.

The continuous production of the isocyanate in a) is effected in a reaction zone by a process known from the prior art. Suitable processes are described, for example, in EP 2 077 150 B1, EP 1 616 857 A1, EP 1 873 142 A1, EP 0 716 079 B1 or EP 0 314 985 B1. However, concentrations and flow rates of the amine and phosgene reactants are preferably chosen such that a molar ratio of phosgene to primary amino groups of 1.1:1 to 30:1, more preferably of 1.25:1 to 3:1, is established in the mixing zone. All processes for the production of an isocyanate in the liquid phase give a crude process product which is divided/separated into a liquid phase (60) comprising, as well as the desired isocyanate, dissolved hydrogen chloride, excess dissolved phosgene and solvent, and a gas phase (70) comprising hydrogen chloride gas, excess gaseous phosgene and gaseous solvent. The invention also encompasses an embodiment in which the crude isocyanate stream 60 obtained, prior to further processing in b), passes through an apparatus for cleavage of carbamoyl chloride.

The further removal of hydrogen chloride and phosgene from the liquid crude isocyanate stream 60 in what is called the dephosgenation column 2100 in b) can be effected by any desired process known from the prior art, preferably as described in DE-A-10260084.

The further removal of solvent from the liquid isocyanate stream 80 thus obtained in what is called the solvent column 2200 in c) can be effected by any desired process known from the prior art, preferably as described in EP 1 854 783 B1.

The removal of phosgene from the gaseous solvent stream 110 thus obtained, preferably after liquefaction thereof in a condenser (2310), in what is called the solvent stripper 2300 in d) can be effected by any desired process known from the prior art, preferably as described in EP 1 854 783 B1.

The removal of solvent from the liquid isocyanate stream 100 obtained in step III) in e), optionally comprising a polymer removal, can be effected by any desired process known from the prior art. Suitable processes are described in EP 1 854 783 A2 and EP 1 506 957 A1, or else in EP 1 371 635 B1.

The absorption of the gaseous streams from steps I), II) and III) in a solvent in what is called the phosgene absorber 2500 in f) can be effected by any desired process known from the prior art, preferably as described in DE-A-10260084 or EP 2 093 215 A1.

The absorption of the HCl gas stream 170 thus obtained in water or dilute hydrochloric acid in what is called the HCl absorption column 2600 for obtaining hydrochloric acid in g) can be effected by any desired process known from the prior art. Preference is given to procedures as described in EP 2 021 275 B1 and EP 1 743 882 B1.

The process step of process offgas treatment in h) can be effected by any process known from the prior art.

The continuous production of phosgene in i) can in principle be conducted by any processes known from the prior art. For the execution of this step of the process according to the invention, it is possible to utilize a "low-temperature combiner" according to EP 1 640 341 B1 or a "high-temperature combiner" according to EP 0 134 506 B1. High-temperature combination (see EP 0 134 506 B1)—which is used with preference—involves converting phosgene by reaction of chlorine with carbon monoxide in tubular reactors containing activated carbon as catalyst with simultaneous exploitation of the heat of reaction obtained for generation of steam.

This is done by reacting, in a first tubular reactor containing granular activated carbon and having a clear tubular diameter of not more than 100 mm, 95% by volume to 98% by volume of the chlorine used with excess carbon monoxide to give phosgene at reaction temperatures exceeding 250° C. The heat of reaction obtained here is removed by evaporative cooling of a liquid that boils at 150° C. to 320° C. or with a non-boiling liquid, the temperature of which is kept at 150° C. to 320° C. at the reactor outlet by means of forced circulation pumps and temperature control. The liquid or vaporous heat carrier leaving the reactor is condensed in a heat exchanger charged with water as cooling medium to generate steam and/or cooled to a temperature below the temperature of the heat carrier at the reactor exit and recycled into the reactor. The reaction gases leaving the reactor are cooled to a temperature of 50° C. to 120° C. and then passed into a second reactor containing granular activated carbon, the temperature of which is set to 50° C. to 100° C. by thermostatic means and in which the conversion is conducted to completion, such that the phosgene leaving the second reactor has a residual chlorine content of less than 50 ppmv. The phosgene exiting at the top of the reactor is condensed as described above.

The inventive procedure for shutdown of one or more plant sections is described in detail hereinafter:

The shutdown of $m_2$, i.e. the mass flow of amine, optionally diluted with solvent, into the mixing unit of the reaction zone from step I), ensures that, during the stoppage which, as described above, is implemented for the purpose of inspection, maintenance, repair and/or cleaning of a section of the production plant or is caused by a shortage of raw material(s) and/or auxiliary/auxiliaries, the reaction in step I) does not continue to take place. It is especially preferable here that, when the supply of amine is stopped, the supply of phosgene and solvent is not simultaneously cut off as well. Instead, it is preferable to cut off the supply of the solvent which serves for dilution of the amine and the phosgene and the supply of phosgene diluted with solvent with a time delay (preferably of at least 15 min, further preferably at least 30 min and more preferably at least 60 min since $m_2$ is zero). This ensures that the amine pipeline, the mixing unit and the reactor are rinsed free of amine Should the stoppage last for longer than 3 hours, phosgene can also be shut down, such that, in that case, only solvent flows through the phosgene pathway into the mixing unit and the reaction space. Once the phosgene pipeline is phosgene-free, the mixing unit can optionally be bypassed and solvent can be run directly into the first reactor. Then the reaction zone of step (I) can be put into circulation mode, meaning that the discharged stream comprising solvent, phosgene and isocyanate is used as input stream for the dephosgenation column from step (II) and thence, as already described, is run through the distillation from step (V), the stripping column from step (VI) and back to the first reactor of the reaction zone in circulation mode. This can advantageously achieve the effect that, firstly, any formation of by-products can be prevented and, secondly, for example, no lumps are formed in the reaction mixture. It is thus possible to efficiently avoid contamination of the desired product, blockage of plant sections, for example of pipelines, valves and pumps, and also caking and the production of reject material.

As already mentioned, it is possible to conduct the isocyanate production in two or more production lines connected in parallel (i.e. plants comprising at least the plant sections from I) to VI)). It is likewise conceivable that only parts of a production line (for example the reactor line comprising the mixing unit 1100 and the reaction space 1200) are replicated and operated in parallel. In such cases, for the inventive configuration of a production stoppage, it is firstly possible to put one or more plant sections out of operation in one production line or reactor line and to operate the other plant sections of this/these production line(s) or reactor line(s), if necessary, in the circulation mode of the invention. Production lines unaffected by the shutdown can continue to be operated. It is likewise possible, in the case of multiple reactor lines operated in parallel within a production line, to continue to operate all reactor lines that are unaffected by a production shutdown and the remaining plant sections in the production line affected. Alternatively, it is also possible in the context of the present invention to stop production in all isocyanate production lines or reactor lines, if necessary, and to convert plant sections that have not been completely shut down to circulation mode simultaneously or in close succession.

The present invention therefore further provides a plant (10000) for preparation of isocyanates (1) in the liquid phase, comprising the following plant sections:

I) a reaction zone (1000) comprising
  I.1) a unit (1020) for providing an amine (2), preferably in the form of an amine solution (20) in a solvent (4),
  I.2) a unit (1030) for providing phosgene (3), preferably in the form of a phosgene solution (30) in a solvent (4),
  I.3) a unit (1040) for providing a solvent (4),
  I.4) a mixing unit (1100) for mixing amine (2) or amine solution (20) with phosgene (3) or phosgene solution (20) and optionally further solvent (4) and
  I.5) a reaction space (1200) arranged downstream of the mixing unit, for conducting the phosgenation, with a separator unit (1210) optionally connected downstream, wherein the reaction space or the separator apparatus have optionally been provided with outlet conduits for a liquid stream (60) and a gaseous stream (70);

II) a distillation apparatus (2100—"dephosgenation column") for separating the liquid stream (60) into a liquid stream (80) and a gaseous stream (90);

III) a distillation apparatus (2200—"solvent column") for separating the liquid stream (80) into a gaseous stream (110) and a liquid stream (100);

IV) a distillation apparatus (2300—"solvent stripper") for separating the gaseous stream (110), preferably after it has been liquefied in a condenser (2310), into a liquid stream (120) and a gaseous stream (130);

V) a distillation apparatus (2400) for obtaining a liquid isocyanate stream (140) from the liquid stream (100), resulting in a gaseous stream (150) comprising secondary components and optionally solvent, optionally comprising an upstream unit for polymer removal (2410—"polymer removal", PMA) for removal of polymeric isocyanate fractions (141);

VI) an apparatus for absorption (2500—"phosgene absorber") of the gaseous streams (70), (90) and (130) in solvent to obtain a liquid stream (160) and a gaseous stream (170);

VII) optionally (and preferably) an apparatus for absorption (2600—"HCl absorption column") of the gaseous stream (170) in water;

VIII) optionally (and preferably) an apparatus for workup of offgas streams (3000), configured for workup of offgas streams at least from VII), preferably for workup of offgas streams from all the plant sections present;

IX) optionally (and preferably) an apparatus (4000) for preparation of phosgene, connected to the unit (1030);

where
the plant (10000) is configured such that, in a shutdown of one or more of plant sections I) to IX), insofar as they are present,
the mass flow rate $m_2$ is reduced to zero and, in at least one of the plant sections that is not being shut down, the output stream of this at least one plant section which is not being shut down
  (i) can be recycled into the respective plant section or
  (ii) can be conducted into a plant section which is upstream or downstream and thence, optionally via further plant sections that have not been shut down, recycled into the original plant section (called "circulation mode").

The configuration of the system for stopping the amine supply on shutdown of one or more plant sections is preferably implemented by process control units. Suitable software and hardware products are commercially available and known to those skilled in the art.

In a preferred embodiment of the present invention, the plant sections may independently be switched to input streams consisting of recycled output streams. In a further preferred embodiment, various plant sections may be switched simultaneously to input streams consisting of recycled output streams. It is preferable here that, in every other plant section which is not being shut down, the output stream, as elucidated further up, can be used as input stream for this or another plant section and hence ultimately be recycled into the original plant section. It is further preferable that every plant section which is not being shut down may also be part of two different circulation modes. If the plant comprises a plant section for phosgene generation 4000 (phosgene generation apparatus, IX), it is preferable that this plant section, in the event of a stoppage of the process, is merely switched off, but not set to circulation mode. In respect of the plant section of the offgas cleaning system 3000 (VIII), this plant section preferably remains in operation in any stoppage of the process (except for total shutdown, for example for an inspection shutdown). In the event of failure of the offgas cleaning system 3000 (VIII), the complete plant with all its plant sections is shut down.

The plant of the invention is elucidated in detail hereinafter:

Preferably, the reaction zone 1000 (I) comprises an amine reservoir tank, a stoppable amine metering conduit and a stoppable solvent metering conduit to the amine/solvent mixer (1020), a pipeline for the amine/solvent mixture to the mixing apparatus for phosgene stream and amine stream (1100), a liquefier (not shown) for the phosgene generated in the phosgene generator (4000), a reservoir tank for preparation of a phosgene/solvent mixture (1030), a stoppable phosgene/solvent metering conduit to the mixing apparatus for phosgene and amine (1100), and a stoppable solvent metering conduit (not shown) into the connection between the mixing apparatus for the phosgene- and amine-containing input streams (1100) and the heatable reaction space (1200) of the reaction zone (1000).

It is preferable to configure and to operate the plant of the invention (especially preferably by means of process control units) in such a way that, on shutdown of one or more plant sections other than the reaction zone I), (at first) only the amine flow into the mixing apparatus of the reaction zone I) is stopped. The amine metering conduit is preferably flushed free of amine with a solvent stream (120) substantially freed of phosgene and isocyanate for at least 10 min (in a preferred configuration of the plant of the invention, corresponding to the flow of one sixth of the amount of solvent which is run through the amine metering conduit per hour at nameplate capacity), preferably at least 20 min (in a preferred configuration of the plant of the invention, corresponding to the flow of one third of the amount of solvent which is run through the amine metering conduit per hour at nameplate capacity). The phosgene/solvent stream (30) preferably continues for 60 min (in a preferred configuration of the plant of the invention, corresponding to the flow of the amount of phosgene/solvent stream which is run through the phosgene metering conduit per hour at nameplate capacity), preferably at least 3 hours (in a preferred configuration of the plant of the invention, corresponding to the flow of three times the amount of phosgene/solvent stream which is run through the phosgene metering conduit per hour at nameplate capacity), in order to assure the conversion of the amine in the reaction zone. If no other user for phosgene is available, it is necessary, if present, also to shut down the phosgene generator (4000) when the amine supply is stopped. If the production stoppage lasts for longer than 12 hours, the phosgene/solvent mixture (30) is then also stopped and the phosgene/solvent metering conduit is purged with a solvent (160) that has been substantially freed of phosgene and isocyanate through the reaction zone I). Until operation has been stopped for 12 hours, the phosgene/solvent stream (30) to the mixing apparatus 1100 is conducted through the reaction space 1200, then firstly via the gas phase (70) to the phosgene absorption (VI) and secondly via the liquid outlet (60) of the reaction space to the dephosgenizer (II) and thence, via the gas phase thereof, likewise to the phosgene absorption (VI). In the phosgene absorption (VI), the collected gas phases are condensed, and residual hydrogen chloride is removed. The liquid phase is conducted to the phosgene dissolution tank 1030 and thence back to the mixing apparatus 1100 of the mixing zone I), which establishes the circulation mode (cf. FIGS. 2 and 3).

The liquid phase from the dephosgenizer (II) is conducted to the solvent distillation (III), and the solvent-containing top product is run via the solvent purification (IV) as liquid phase which has been very substantially freed of phosgene and isocyanates to the solvent tank (1040), likewise as a circulation stream back to the mixing apparatus (1100) of the reaction zone I) (FIG. 4), while the gaseous phosgene- and solvent-containing phase from the solvent cleaning (IV) to the phosgene absorption (VI) is likewise circulated.

When working on the mixing apparatus, this can be shut down and the circulation mode with the solvent from the solvent cleaning (IV) can be conducted back to the solvent cleaning (IV) via the solvent tank (1040) and then, beyond the shut-off mixing apparatus, into the intake of the reaction space 1200 and via the dephosgenation column (II) and the solvent distillation (III). Evaporated components of the circulated solvent are run into the phosgene dissolution tank (1030) via the gas phase of the dephosgenation column (II) and the liquid phase of the phosgene absorber (VI).

In addition, it is preferable that the distillation apparatus 2100 (II) of the plant of the invention, in which the crude isocyanate (60) from I) is separated into a liquid organic phase (80) comprising crude isocyanate and solvent and a gaseous phase (90) comprising phosgene and traces of solvent and hydrogen chloride comprises a dephosgenation column with evaporator.

Figure 4:
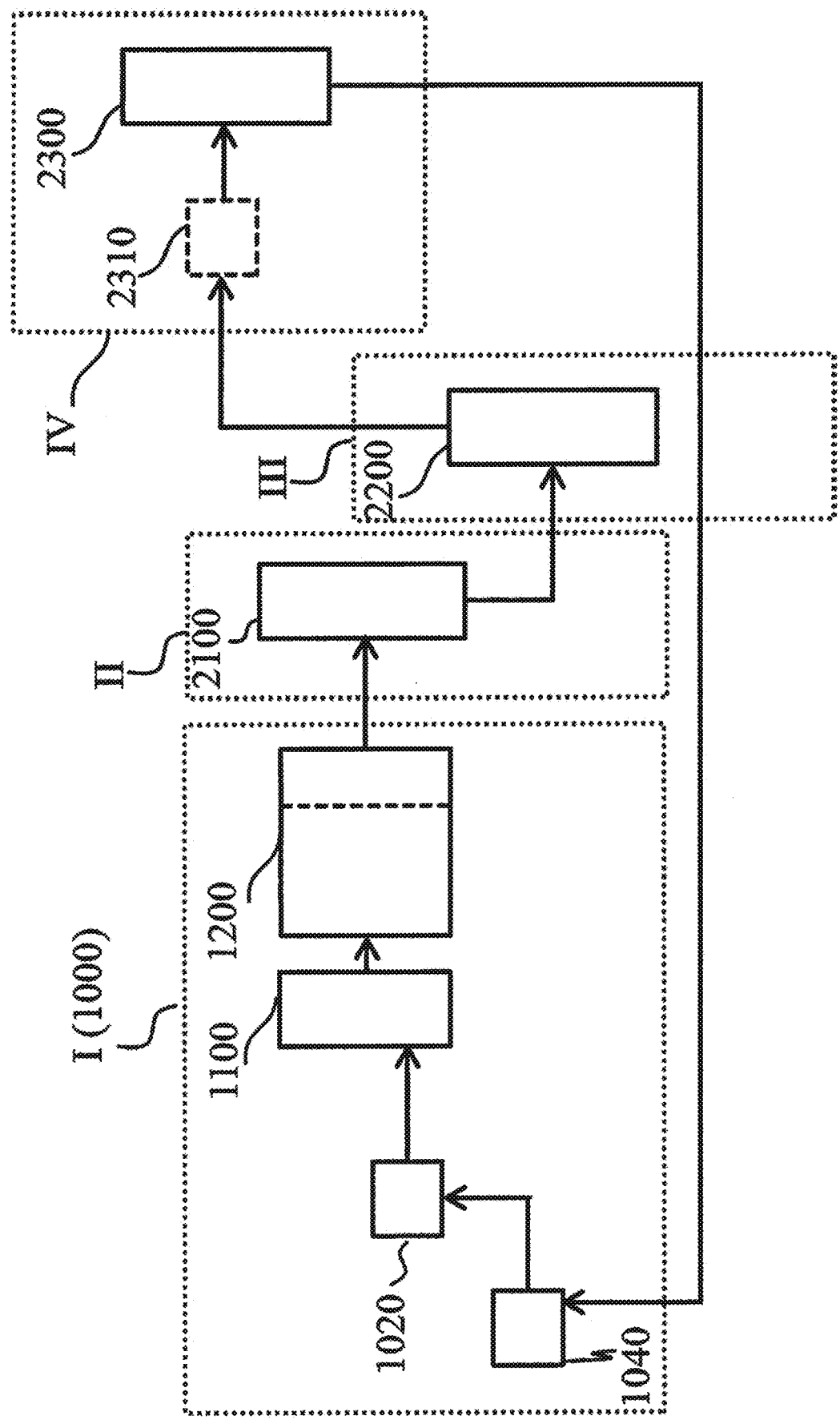
FIG. 4 illustrates a process flow for an embodiment of the invention in circulation mode in which the reaction zone (I), the dephosgenation column in the distillation apparatus (II), the solvent column in the distillation apparatus (III), and the solvent cleaning apparatus (IV) operate together to establish a circulation mode from the reaction zone (I) to the dephosgenation column (II), to the solvent column (III) to the solvent cleaning apparatus (IV) to the reaction zone (I).

The plant of the invention is preferably configured (especially preferably by means of process control units) and is preferably operated such that, on shutdown of one or more plant components other than the dephosgenation column (II), this plant section still remains in operation in order to accept the liquid output from the reaction space 1200 until operation has been stopped for 12 hours, in the course of which the gas phase which becomes increasingly hydrogen chloride-free after stoppage of the amine stream is circulated back to the dephosgenation column (II) via the phosgene absorber (VI), the phosgene dissolution tank 1030, the mixing unit 1100 and the reaction space 1200. In the course of this, the liquid organic phase which becomes increasingly crude isocyanate-free after stoppage of the amine stream is circulated via the distillation apparatus (III), the solvent cleaning (IV) and the solvent tank (1040) and thence via the mixer and the reaction space into the dephosgenation column (II) (FIG. 4).

Preferably, the distillation apparatus 2200 (III) of the plant of the invention, in which the crude isocyanate (80) from II) is separated into a liquid phase (100) comprising crude isocyanate and solvent and a gaseous phase (110) comprising solvent and residual phosgene, comprises two distillation columns connected in series (not shown in FIG. 1) connected to a vacuum system and operated under reduced pressure by means of a vacuum system and vented into the apparatus for offgas cleaning (XIII), each of which has an evaporator, a vapor condensation system and a scrubber which is supplied with solvent in order to prevent entrainment of crude isocyanate into the solvent cleaning (IV).

The plant of the invention is preferably configured (especially preferably by means of process control units) and is preferably operated such that, on shutdown of one or more plant components other than the distillation apparatus (III), the latter still remains in operation under reduced pressure in order to be able to accept the liquid output from the distillation apparatus (II) until operation has been stopped for 12 hours, in the course of which the gas phase that has been freed of traces of isocyanate is condensed and circulated back to the distillation apparatus (III) via the solvent cleaning (IV) and the solvent tank (1040) connected thereto, via the mixer and the reaction space into the separation apparatus (II). In the course of this, the liquid organic phase is circulated back into the distillation apparatus (III) via a crude isocyanate intermediate storage tank provided solely for a circulation mode of step III) and/or step II) and/or step V), and thence into the intake line between the distillation apparatus (II) and the distillation apparatus (III). Alternatively, the liquid organic phase can be circulated back into the distillation apparatus (III) via the first column (2410) of the isocyanate cleaning (V), via the crude isocyanate intermediate storage tank and thence into the intake line between the distillation apparatus (II) and the distillation apparatus (III).

Preferably, the distillation apparatus 2300 (IV) of the plant of the invention, in which the precleaned solvent (110) from step III) is freed of residual phosgene, comprises a stripping column provided with a vacuum system and having a pump receiver and evaporator, a pump receiver for the distillate discharge, and a vapor condensation system which is operated under reduced pressure by means of a vacuum system and is vented into the apparatus for offgas cleaning (VIII).

The plant of the invention is preferably configured (especially preferably by means of process control units) and is preferably operated such that, on shutdown of one or more plant components other than the distillation apparatus (IV), the latter still remains in operation under reduced pressure in order to be able to accept the vapors condensed in 2310 from (III) until operation has been stopped for 12 hours, in the course of which the solvent that has been freed of residues of phosgene is circulated back to the distillation apparatus (IV) via the solvent tank (1040), the mixing unit 1100 and the reaction space 1200 into the distillation apparatus (II) and thence via the distillation apparatus (III) (cf. FIG. 4). Alternatively, the solvent that has been freed of residues of phosgene can be circulated back into the solvent cleaning (IV) via the distillation apparatus (III), going via the crude isocyanate intermediate storage tank from (III) into the intake conduit between the distillation apparatus (II) and the distillation apparatus (III).

In the distillation apparatus (V) of the plant of the invention, the crude isocyanate (100) from step III) is freed of traces of solvent and any secondary components and separated into the isocyanate(s) of the desired purity and composition. The distillation apparatus (V) comprises at least the distillation apparatus 2400 and, in particular embodiments, likewise the unit for removal of polymeric isocyanate fractions 2410.

In a particular configuration of the invention which is especially suitable for the preparation of di- and polyisocyanates of the diphenylmethane series (collectively MDI hereinafter), the distillation apparatus (V) comprises the unit for polymer removal (2410). In this embodiment, the crude isocyanate from III) (stream 100 in FIG. 1) is conducted via a feed pump (not shown in the figures) into this first distillation unit (2410) with a vacuum system (conduit drawn as a solid line for stream 100 in FIG. 1; conduit drawn as a dotted line for stream 100 in FIG. 1 is absent in this embodiment). The unit (2410) also comprises an evaporator (not shown in the figures), a packed column, a pump receiver for the reflux stream onto the column packing (not shown in the figures), a vent (not shown in the figures) into the apparatus for offgas cleaning (VIII), a vapor condensation system having a vapor draw for residual traces of solvent (likewise not included in the figures), a distillate withdrawal point for monomeric isocyanate fractions 142 (i.e., in the case of preparation of di- and polyisocyanates of the diphenylmethane series, for methylene diphenyl diisocyanate [MMDI—"monomeric MDI"]). The unit (2410) also comprises a steam generator and a circulation pump (neither shown in the figures) to the product tank (2430) for accepting the bottoms output stream from the unit for polymer removal (2410). This bottoms output stream comprises the polymeric isocyanate fractions (141), i.e., in the case of preparation of di- and polyisocyanates of the diphenylmethane series, a mixture of polymethylene polyphenylene polyisocyanate [PMDI—"polymeric MDI"] and methylene diphenyl diisocyanate [MMDI—"monomeric MDI"].

The distillation apparatus (V) in this embodiment further comprises a pump receiver with a circulation pump (not shown in the figures), into which are fed the monomeric isocyanate fractions (142) from the distillate withdrawal point of the unit for polymer removal (2410). Thence, the stream (142) is guided into a second distillation apparatus (2400) for obtaining additional isocyanate compositions and isocyanate qualities, i.e., in the case of the preparation of di- and polyisocyanates of the diphenylmethane series which has been mentioned by way of example, for obtaining (polymer-free) methylene diphenyl diisocyanate fractions (MMDI fractions). The apparatus for cleaning and optionally also separating the monomeric isocyanate fractions (2400) need not, as shown in the figures, consist only of a single distillation column. Instead, 2400, in particular embodiments, may also represent two or more, preferably 4 to 10, distillation columns connected in series and optionally also partly in parallel, in which case each of these distillation columns is equipped as described for the unit 2410. In these particular embodiments, in that case, multiple fractions (with different isomer composition) of purified isocyanate stream 140 are obtained (for instance, in the case of the preparation of di- and polyisocyanates of the diphenylmethane series mentioned by way of example, a fraction 140-1 composed predominantly of diphenylmethane 4,4'-diisocyanate and a fraction 140-2 composed of a mixture of essentially diphenylmethane 2,4'- and 4,4'-diisocyanate). Purified isocyanate 140 (or 140-1, 140-2, . . . ) is guided into the connected product tank 2440 (in the case of multiple isocyanate fractions 140-1, 140-2, . . . into multiple product tanks 2440-1, 2440-2, . . . ). Possible configurations of the apparatus 2400 in the case of di- and polyisocyanates of the diphenylmethane series are described in DE 31 450 10 A1, FIG. 2 and FIG. 3. The restriction to a single distillation column 2400, a single vapor stream 150 and a single product tank 2440 in the figures is thus due merely to simplification of the drawing. The uncondensable vapors (150) from the distillation apparatus 2400 are guided into the offgas system.

It is also possible to execute the distillation apparatus (2400) as a dividing wall column, in which case the various monomeric isocyanate fractions (in the case of preparation of di- and polyisocyanates of the diphenylmethane series, fractions having the isomers of MMDI in different composition) are obtained at various points in the column. It is also possible to connect multiple dividing wall columns in series, optionally also combined with columns without a dividing wall, as described in EP 1 475 367 B1.

In another particular embodiment of the invention which is especially suitable for the preparation of tolylene diisocyanate (TDI), the unit (2410) is dispensed with (in other words, the stream 100 is guided directly into the distillation apparatus 2400; cf. the conduit shown by a dotted line for stream 100 in FIG. 1), and the distillation apparatus (2400) is configured as a dividing wall column. Purified isocyanate (140), i.e. pure TDI in the case of preparation of TDI, is withdrawn from the column (2400) as a sidestream, while a mixture of polymeric components ("residue") and monomeric isocyanate (TDI in the case mentioned by way of example) is obtained at the bottom of the column as stream (143). In this embodiment, the removal of polymeric isocyanate fractions is thus integrated into the distillation apparatus 2400 in apparatus terms. It is possible to recover monomeric isocyanate from stream 143 by concentration. Alternatively, stream 143 can also be hydrolyzed to recover the corresponding amine. A purely thermal utilization of stream 143 by combustion is likewise possible. There is no stream 143 in the sense of a residue stream as outlined above in the embodiment comprising the polymer removal 2410 as described further up (it is of course also possible in this embodiment comprising the polymer removal 2410 for bottom streams to occur in the apparatus 2400; in that case, however, these comprise high-boiling monomer fractions 140 and/or high-boiling impurities—the polymeric isocyanate fractions are removed as stream 141 in 2410).

It is preferable to configure and to operate the plant of the invention (especially preferably by means of process control units) in such a way that, on shutdown of one or more plant sections other than the distillation apparatus (V), the vacuum is still maintained and the steam supply to the evaporator of the distillation column is stopped preferably 20 minutes after stoppage of the amine supply to the reaction zone I), more preferably 40 minutes (according to the production load) after stoppage of the amine supply to the reaction zone I), in order to be able to accept the output from (III) until operation has been stopped for 12 hours. In this case, the cooling output from the distillation column, rather than going to the end product tank, is switched to circulation mode and circulated back to (V) via the distillation apparatus (III), going via the crude isocyanate intermediate storage tank from (III) and thence into the intake line between distillation apparatus (II) and the distillation apparatus (III).

Preferably, the absorption apparatus 2500 (VI), in which the vapors from the reaction zone I) (70), the dephosgenizer II) (90) and the solvent cleaning IV) (130) are collected, and in which the combined vapors are separated into a liquid organic phase (160) comprising phosgene and solvent and a gaseous phase (170) comprising hydrogen chloride and traces of phosgene and solvent, comprises multiple heat exchangers connected in series that are operated with cooled solvent as cooling medium, in which the gaseous phosgene and solvent from the three collected vapor streams are cooled and condensed, and a solvent-operated scrubbing column in which traces of phosgene and solvent are scrubbed out of the gaseous hydrogen chloride that remains.

It is preferable to configure and to operate the plant of the invention (especially preferably by means of process control units) in such a way that, on shutdown of one or more plant sections other than the absorption apparatus (VI), operation of the apparatus VI, as described above for the reaction zone in step I), is continued in circulation mode, in the course of which the hydrogen chloride concentration in the vapors from steps I), II) and IV) decreases constantly since the amine stream has been stopped in accordance with the invention and only amine remaining in the reaction zone I) is being depleted by reaction to give crude isocyanate and hydrogen chloride. The cooling by the heat exchangers is maintained. The application of solvent to the scrubbing column of the absorption apparatus 2500 is constantly reduced in terms of amount and, after 12 hours, is likewise stopped with the shutdown of the entire plant.

In addition, it is preferable that the absorption apparatus 2600 (VII) of the plant of the invention, in which the gaseous hydrogen chloride stream (170) still containing traces of phosgene and solvent is absorbed as hydrochloric acid with HCl-containing water (not shown) and fresh, cold steam condensate (180) in an exothermic operation, comprises an absorption column 2600, a connection to the apparatus for offgas cleaning (VIII) and a bottoms discharge cooler. The traces of solvent and phosgene are conducted by the top of the absorption column (stream 200) into the apparatus for offgas cleaning (VIII). The HCl-containing water is withdrawn from the apparatus for offgas cleaning (VIII) comprising an activated carbon-operated tower to which a trickle of fresh water is applied under reduced pressure, and to which the absorption apparatus VII) is also connected. For intermediate storage of the hydrochloric acid, there is a hydrochloric acid tank (2610) linked to the absorption column 2600, which is utilized in the regular operation of the plant. In addition, there is a further tank (2620) containing weak hydrochloric acid linked to the absorption column 2600, which accepts the HCl-containing water from the apparatus for offgas cleaning 3000 (VIII). After the stoppage of the amine stream ($m_2$=0), the formation of hydrogen chloride and hence the production of hydrochloric acid abates.

It is preferable to configure and to operate the plant of the invention (especially by means of process control units) in such a way that, on shutdown of one or more plant sections other than the absorption apparatus VII, the absorption apparatus remains in operation over the entire operation stoppage, in order to be put into circulation mode together with the process offgas destruction system, which likewise remains in operation over the entire production stoppage, via the output from the absorption apparatus to the weak hydrochloric acid-containing vessel and via the output thereof to the absorption apparatus.

Preferably, the optional apparatus for offgas cleaning 3000 (VIII) ("process offgas destruction") of the plant of the invention, in which the phosgene-containing process offgases from the vacuum systems from at least step VII), preferably from all plant sections with vacuum systems, and also the inert gases from the pressure-maintaining systems and the offgases from the tank blanketing systems are destroyed, comprises an apparatus operated under reduced pressure with activated carbon and having a vent operated via a ventilator to a thermal waste air cleaning system ("TAR").

It is preferable to configure and to operate the plant of the invention (especially preferably by means of process control units) in such a way that, on shutdown of one or more plant sections other than the process gas destruction (VIII), the process gas destruction system must absolutely remain in operation in order to accept and process, over the entire operation stoppage, the inert gases from the pressure-maintaining systems and the offgases from the tank blanketing systems, wherein the liquid phase from the hydrogen chloride absorption column 2600 (VII), rather than going to the hydrochloric acid tank, is diverted to the vessel for the weak hydrochloric acid, wherein the weak hydrochloric acid is circulated via the activated carbon-operated apparatus of the process offgas destruction system, through the hydrogen chloride absorption column and back to the vessel containing the weak hydrochloric acid. An important basis for the process is that the activated carbon-operated tower of the process offgas destruction system, in the operation of the isocyanate plant, is always the first to be put into operation and the last to be shut down.

Preferably, the optional phosgene generation apparatus 4000 (IX) of the plant of the invention, in which fresh phosgene is prepared from chlorine (220) and carbon monoxide (230) as feedstocks, comprises a mixing apparatus for the feedstocks, an apparatus equipped with activated carbon as catalyst with metering conduits for the feedstock mixture, a cooling circulation system and a phosgene liquefier (not shown) with an exit line to the phosgene dissolution tank (1030) in which the phosgene/solvent mixture for the phosgenation in reaction zone I) is prepared. The offgas from the phosgene liquefier is preferably connected to the TAR.

It is preferable to configure and to operate the plant of the invention (especially preferably by means of process control units) in such a way that, on shutdown of one or more plant sections other than the phosgene generator IX), the latter is likewise shut down with the stoppage of the amine supply to the reaction zone I).

These preferred embodiments are of course merely representative examples of a multitude of possible circulation modes, the exact configuration of which depends on the specific characteristics of a production plant, but can be matched to these specific circumstances in a simple manner in the context of the present invention. However, it is a feature common to all conceivable circulation modes that, after the residual amounts of amine present in apparatuses and pipelines have reacted, no product (isocyanate 1) leaves the plant if it is a single-line isocyanate production plant.

Should two or more isocyanate reactor lines be operated in parallel, it would be possible but not obligatory for product to leave the plant when, for example, the plant is being run with partial load.

In the system of the invention and the process of the invention, it is possible here for any plant section to be set to circulation mode, for example by manual means.

In a preferred embodiment, the switching to circulation mode, the startup and the monitoring of all steps are effected via a central control system which especially preferably comprises process control units.

The present invention further provides a process for operating a plant for preparation of isocyanates in the liquid phase, comprising the following plant sections:
I) a reaction zone (1000) comprising
   I.1) a unit (1020) for providing an amine (2), preferably in the form of an amine solution (20) in a solvent (4),
   I.2) a unit (1030) for providing phosgene (3), preferably in the form of a phosgene solution (30) in a solvent (4),
   I.3) a unit (1040) for providing a solvent (4),
   I.4) a mixing unit (1100) for mixing amine (2) or amine solution (20) with phosgene (3) or phosgene solution (20) and optionally further solvent (4) and
   I.5) a reaction space (1200) arranged downstream of the mixing unit, for conducting the phosgenation, with a separator unit (1210) optionally connected downstream, wherein the reaction space or the separator apparatus have optionally been provided with outlet conduits for a liquid stream (60) and a gaseous stream (70);

II) a distillation apparatus (2100—"dephosgenation column") for separating the liquid stream (60) into a liquid stream (80) and a gaseous stream (90);

III) a distillation apparatus (2200—"solvent column") for separating the liquid stream (80) into a gaseous stream (110) and a liquid stream (100);

IV) a distillation apparatus (2300—"solvent stripper") for separating the gaseous stream (110), preferably after it has been liquefied in a condenser (2310), into a liquid stream (120) and a gaseous stream (130);

V) a distillation apparatus (2400) for obtaining a liquid isocyanate stream (140) from the liquid stream (100), resulting in a gaseous stream (150) comprising secondary components and optionally solvent, optionally comprising an upstream unit for polymer removal (2410—"polymer removal", PMA) for removal of polymeric isocyanate fractions (141);

VI) an apparatus for absorption (2500—"phosgene absorber") of the gaseous streams (70), (90) and (130) in solvent to obtain a liquid stream (160) and a gaseous stream (170);

VII) optionally (and preferably) an apparatus for absorption (2600—"HCl absorption column") of the gaseous stream (170) in water;

VIII) optionally (and preferably) an apparatus for workup of offgas streams (3000), configured for workup of offgas streams at least from VII), preferably for workup of offgas streams from all the plant sections present;

IX) optionally (and preferably) an apparatus (4000) for preparation of phosgene, connected to the unit (1030);
where
(i) in the event of a production stoppage the following steps are run:
   (i) stopping the feed of amine (2) into the mixing unit 1100;
   (ii) if present, switching of the apparatus (4000) for preparation of phosgene;
   (iii) reducing the phosgene feed into the mixing unit (1100), preferably to a value in the range from 10% to 50% of the phosgene feed in regular operation;
   (iv) reducing the solvent feed into the mixing unit (1100), preferably to a value in the range from 10% to 50% of the solvent feed in regular operation, preferably by reducing the solvent feed into the units 1020 and 1030;
   (v) running at least one plant section such that the output stream from the respective plant section
     (v)(i) is recycled into the respective plant section or
     (v)(ii) is conducted into a plant section which is upstream or downstream and thence, optionally via further plant sections that have not been shut down, recycled into the original plant section,
   (called "circulation mode").

If the production stoppage is the consequence of the pending shutdown of one or more plant sections I) to IX), insofar as they are present, the following steps are run after step (v):

(vi) shutting down at least one plant section;

(vii) if necessary, opening the at least one plant section that has been shut down in step (vi);

(viii) conducting a maintenance, cleaning and/or repair measure in the at least one plant section that has been shut down in step (vi);

(ix) if necessary, closing and optionally inertizing the at least one plant section shut down in step (vi).

The plant for the process here is preferably the plant according to the present invention. By this process of the invention, it is advantageously possible to operate the plant in circulation mode in the event of the above-described stoppages (shutdown of individual plant sections) and hence to achieve the advantages and effects of the invention. Very particularly advantageously and therefore preferably, in step (v), very substantially all the plant sections that can be switched to circulation mode and are not affected in any way by the production shutdown are put into circulation mode, but operation of the apparatus for processing of offgas streams 3000 is continued and the apparatus 4000 for phosgene generation is excluded from the circulation mode.

In a preferred embodiment, the process, on shutdown of at least one plant section, comprises the following further steps:

(x) starting up the at least one plant section shut down in step (vi), (xi) if present, starting up the apparatus 4000 for phosgene production, (xii) starting, preferably in this sequence, the supply of solvent, phosgene and amine in the reaction zone 1000 (I).

In another embodiment, which is advantageous when there is merely a shortage of raw material but no maintenance operations are pending, in step (v), all plant sections, preferably with the exception of the phosgene generator 4000 which is preferably shut down as described further up, are operated in such a way that the output stream from the respective plant section is used as input stream for the respective plant section, or in that the output stream from the respective plant section can be used as input stream for a plant section upstream or downstream and, in circulation mode, the output stream from this plant section is returned as input stream for the original plant section, wherein the circulation mode can also be effected over multiple plant sections and one plant section can also be incorporated into more than one circulation mode. In this case, step (v) is followed by the following steps:

xiii) waiting for feedstocks or auxiliaries and, as soon as these have arrived, (xiv) starting, preferably in this sequence, the supply of solvent, phosgene and amine in the reaction zone 1000 (I).

What is to be described hereinafter by way of example is the setting of the entire plant (except for the process offgas system VIII, which remains in operation, and the phosgene generation IX, which is shut down) to circulation mode and, likewise by way of example, the restarting of the plant from circulation mode to normal operation. In a differing manner, it is of course also possible to operate only particular plant sections I to VII in circulation mode and to shut down the others, for example for maintenance operations.

In the first step, the supply of amine to the reaction zone 1000 is stopped.

In the second step, if present, the phosgene preparation is shut down, and the rest of the plant is gradually put into circulation mode. If phosgene is not being prepared in the plant itself but sourced from an external source, the supply from this source is stopped.

In the third step, for up to 3 hours, but for at least 1 hour, running of the phosgene/solvent mixture 30 and the solvent 4 of the amine/solvent mixture 20 into the mixing unit 1100 and thence into the reaction space 1200 and the dephosgenation column 2100 is continued for residual conversion of the amine still present and for dilution of the reaction solution in the reaction zone.

Figure 2:
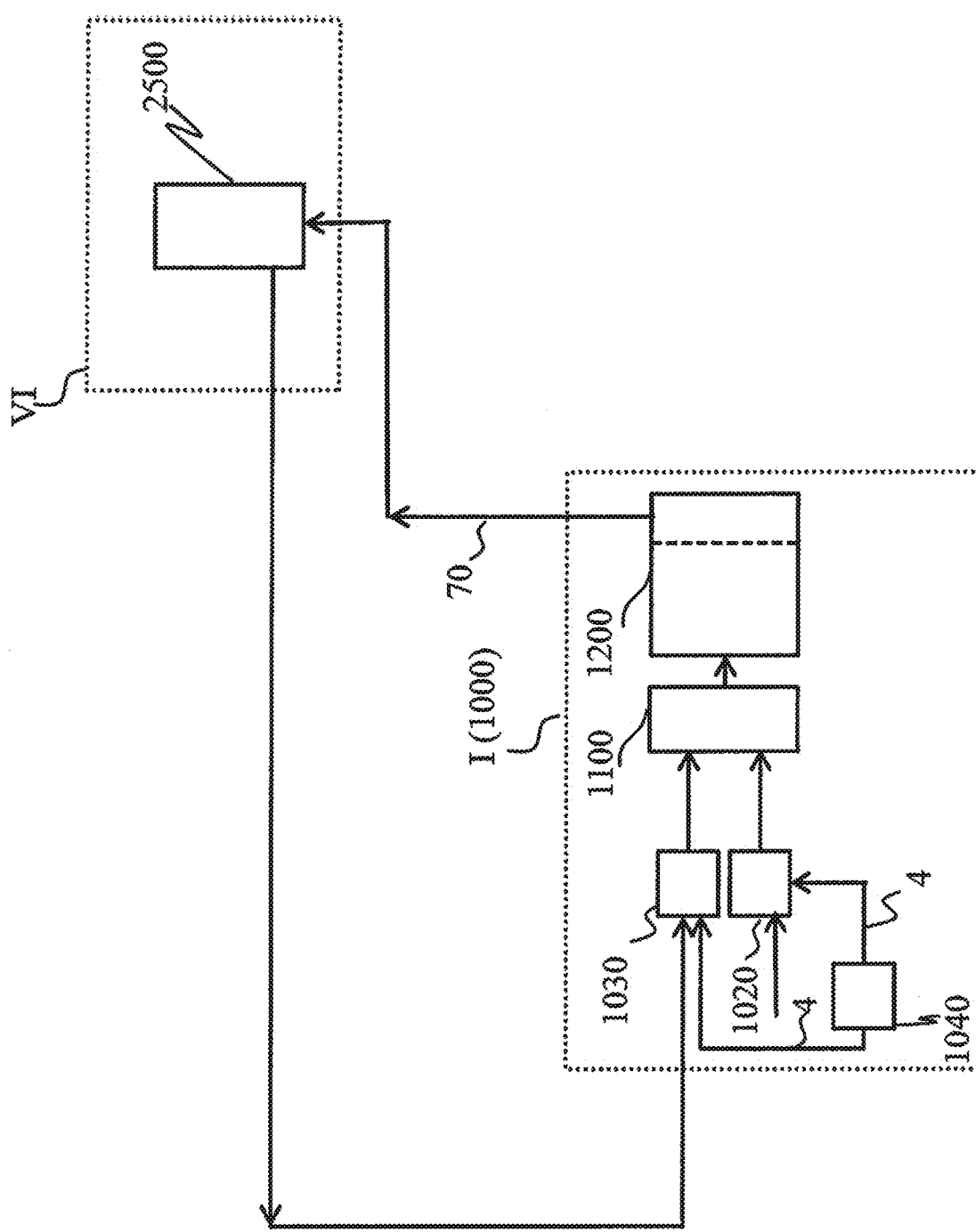
FIG. 2 illustrates the process flow for an embodiment of the invention in circulation mode in which the reaction zone (I) and the phosgene absorber (VI) operate together to establish a circulation mode from the reaction zone (I) to the phosgene absorber (VI) to the reaction zone (I).

The solvent supply to the phosgene pathway and the amine pathway continues, and the reaction zone (I) is charged via the phosgene dissolution tank (1030) with phosgene-containing solvent from the phosgene absorber (VI), and hence a circulation mode I)→VI)→I) is established (cf. FIG. 2).

Figure 3:
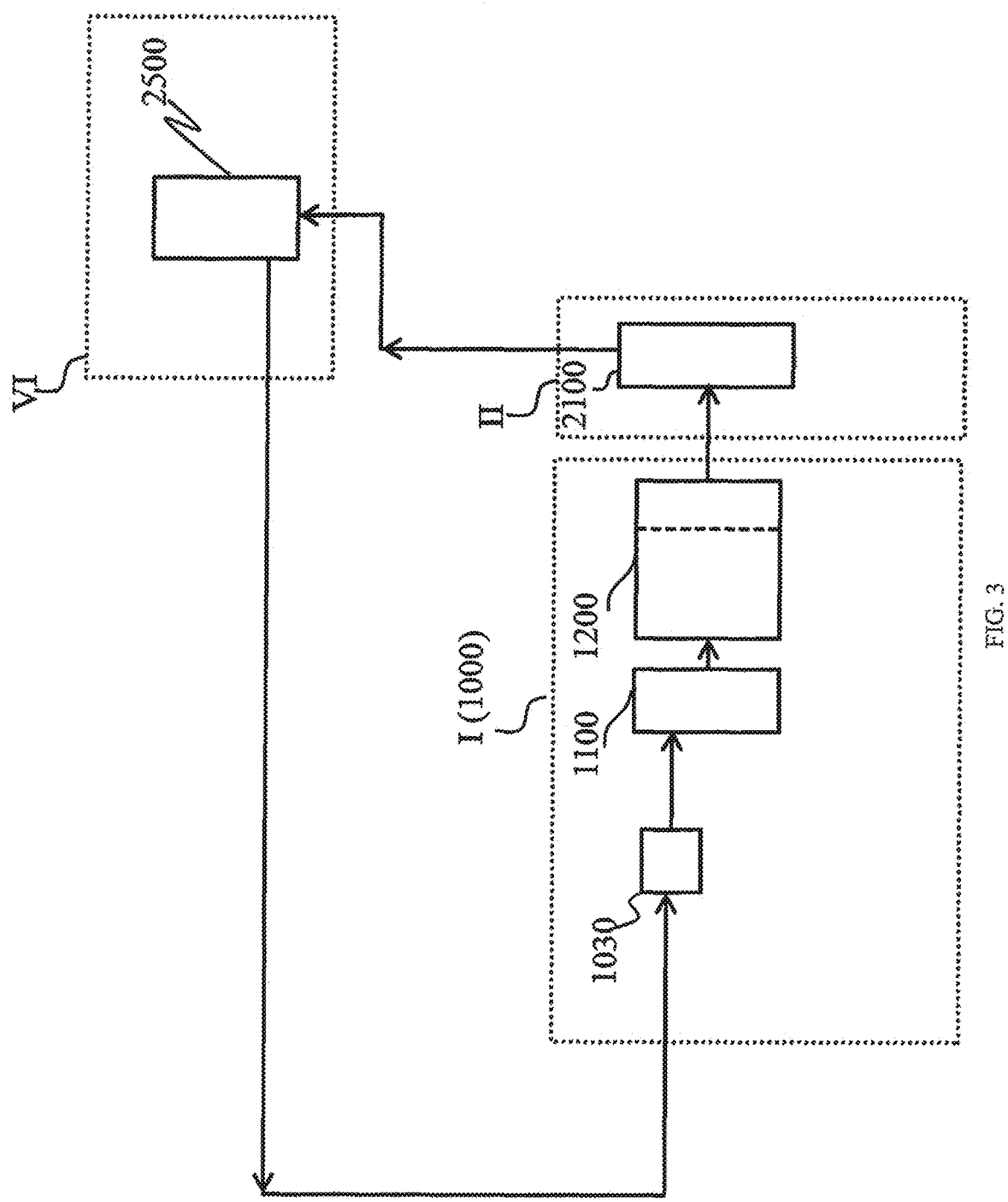
FIG. 3 illustrates a process flow for an embodiment of the invention in circulation mode in which the reaction zone (I), the dephosgenation column (II), and the phosgene absorber (VI) operate together to establish a circulation mode from the reaction zone (I) to the dephosgenation column (II) to the phosgene absorber (VI) to the reaction zone (I).

At the same time, the reaction zone (I) is charged via the phosgene dissolution tank 1030 with phosgene-containing solvent from the phosgene absorber (VI) and the dephosgenation (II), and hence a circulation mode I)→II)→VI)→I) is established (cf. FIG. 3).

At the same time, the reaction zone (I) is put into circulation mode with phosgene-containing solvent via the dephosgenation (II), the solvent distillation (III), the solvent cleaning (IV), the solvent tank (1040) and the unit 1020 (into which no more amine 2 is being fed at this time) back to the mixer (1100) of the reaction zone (cf. FIG. 4) or to the connection of the mixer to the reaction space 1200 (not shown) (circulation mode I)→II)→III)→IV)→I)).

Figure 5:
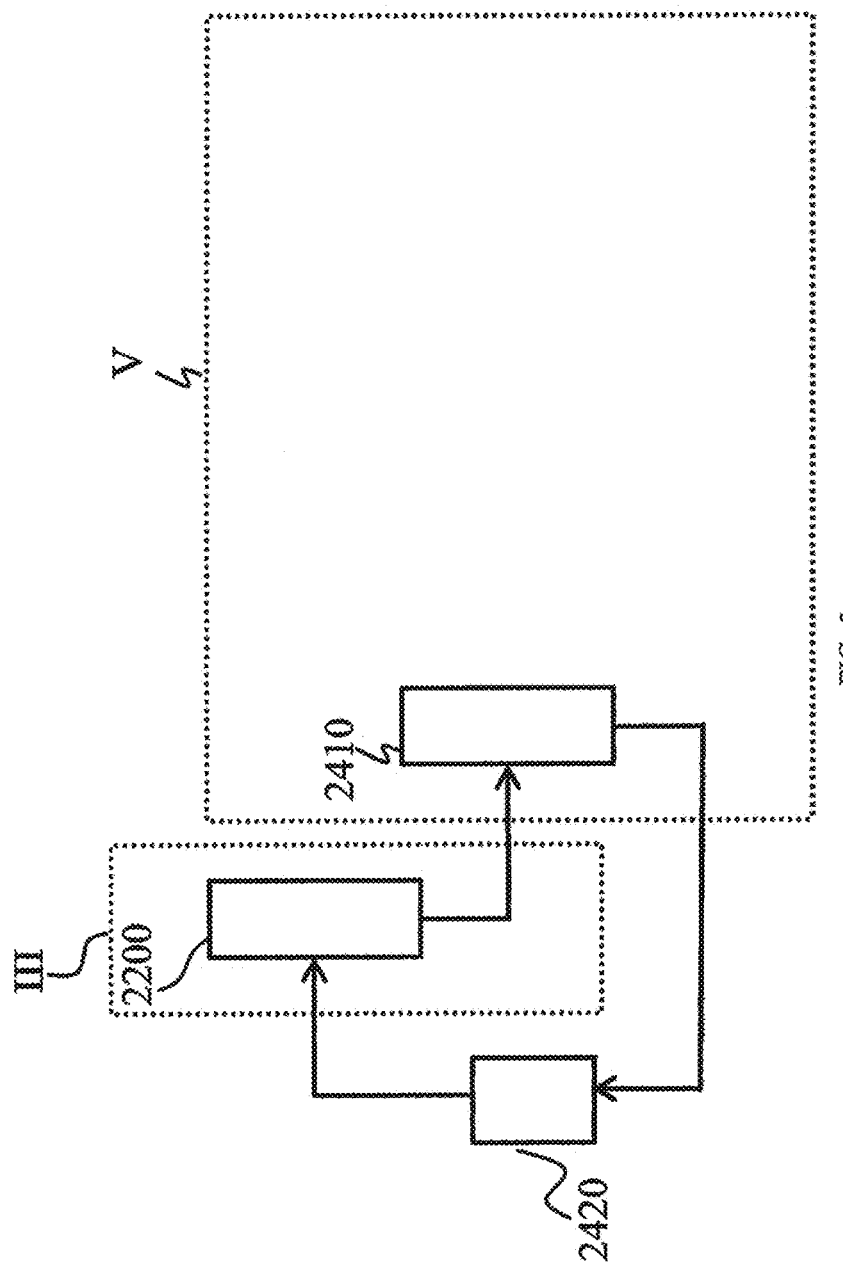
FIG. 5 illustrates a process flow for an embodiment of the invention in circulation mode in which the solvent distillation (III) and the distillation apparatus for the removal of the polymeric isocyanate operate together to establish a circulation mode from the solvent distillation (III) to the distillation apparatus for removal of polymeric isocyanate (V) to the solvent distillation apparatus (III).

At the same time, the dilute crude isocyanate from the solvent distillation (III) is circulated via the distillation of the crude isocyanate (V) (without heating) through the first distillation column 2410 into the crude polymeric isocyanate tank (2420) back to the intake conduit of the solvent distillation (III) (circulation mode III) V)→III); cf. FIG. 5).

Figure 6:
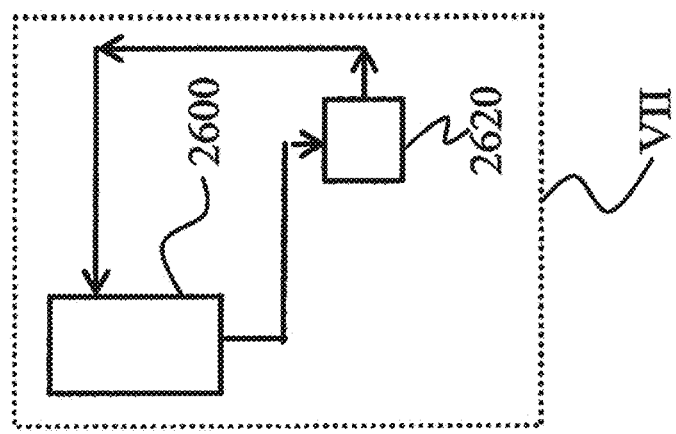
FIG. 6 illustrates a process flow for an embodiment of the invention in circulation mode in which the apparatus for absorption of hydrogen chloride (VII) and the weak acid tank (VII) operate together to establish a circulation mode within the hydrogen chloride absorption (VII).

At the same time, the offgas pathway from the phosgene absorber (VI) to the hydrogen chloride absorption (VII) and thence to the process offgas destruction (VIII) is left open and the hydrogen chloride absorption with weak hydrochloric acid via the weak acid tank (2620) is set to circulation mode (circulation VII) VII); cf. FIG. 6).

After passing through these steps, all the plant sections apart from VIII (process offgas destruction) and IX (phosgene generation) are in circulation mode. It is now possible to conduct maintenance operations on the phosgene generator, for example, or else simply to get through waiting periods resulting from raw material shortage without having to completely shut down the entire plant for the purpose.

In the case of maintenance operations, the phosgene generator (or, if another plant section is affected and therefore only parts of plant sections I to VIII are being operated in circulation mode, this said plant section is emptied, cleaned and, if appropriate, opened for the pending measure. Then the maintenance measure is conducted and the phosgene generator (or the other plant section) is closed again, inertized if appropriate, and filled with auxiliaries and feed materials and prepared for restarting.

During the circulation mode, the vacuum system of solvent distillation and solvent stripper is maintained. Heating of the reaction zone, dephosgenizer, solvent distillation and solvent cleaning is continued. The process offgas system remains in operation.

The restarting of the plant from circulation mode can proceed, for example, as follows:

The vessels and apparatuses are laden with dilute product solution. The vacuum system of solvent distillation (III) and solvent stripper (IV) is running. The reaction zone (I), the dephosgenizer (II), the solvent distillation (III) and the solvent stripper (IV) are heated, and the process offgas system is running. In order to start up the plant again, the phosgene preparation (IX) is started up first.

As soon as phosgene is available in a sufficient amount, secondly, the phosgene solution in the phosgene/solvent tank (1030) is concentrated.

Then, thirdly, the amine pathway is opened. The phosgenation reaction starts immediately to form crude isocyanate and hydrogen chloride. Then the operating segment of the reaction zone has been started up and the vapors (70) from the reaction zone 1200 (or the downstream separation apparatus 1210), comprising phosgene, hydrogen chloride and solvent, are guided to the phosgene absorber (IV), while the liquid phase (80) comprising crude isocyanate, solvent and phosgene is guided to the dephosgenizer (III).

As soon as the vapors from (I) arrive in the phosgene absorber (VI) comprising a separation apparatus, three vapor conduits for the vapors (70, 90 and 130), a discharge conduit for the liquid phase (160) and an outgoing conduit (170) to the hydrogen chloride absorption, the combined fresh vapors from the reaction zone (I), the dephosgenizer (II) and the solvent stripper (IV) are separated into a liquid organic phase (160) comprising phosgene and solvent, which runs into the phosgene dissolution tank (1030) from step I), and a gaseous phase (170) comprising hydrogen chloride with traces of solvent and phosgene, which is conducted into the hydrogen chloride absorption (VII). The gas phase from the hydrogen chloride absorption (200) is guided into the process offgas destruction (VIII).

As soon as the liquid phase from (VI) arrives in the hydrogen chloride absorption (VII) comprising an absorption apparatus, a heat exchanger for cooling the liquid phase, a heat exchanger for condensing the gas phase, a gas supply conduit, two metering conduit for the aqueous phases, a hydrochloric acid storage tank and a storage tank for weak hydrochloric acid with appropriate conduits, the hydrogen chloride gas from the gaseous phase from (VI) is absorbed as hydrochloric acid with acidic water from step (VII) and additional condensate water (180) in an exothermic reaction and run into the hydrochloric acid tank (2610). The offgas 200 goes to the process offgas destruction (VIII).

As soon as the reaction solution (60) from (I) is pumped into the dephosgenation (II) comprising a metering conduit for crude isocyanate, a separating apparatus and a heat exchanger, the reaction solution is separated into a gaseous phase (90) comprising phosgene, solvent and hydrogen chloride, which is conducted into the phosgene absorption (VI), and a liquid phase (80) comprising crude isocyanate, solvent and traces of phosgene, which is pumped into the solvent distillation (III).

As soon as the crude isocyanate 80 from (II) is pumped into the solvent distillation (III) comprising a distillation column with a vacuum system, a pump receiver for the mixture of crude isocyanate and solvent, a heat exchanger for this mixture, a separating apparatus for separation of solvent and crude isocyanate, and a heat exchanger for condensation of solvent vapors, the crude isocyanate (80), in the first step, is freed of the majority of solvent and traces of phosgene, and the latter is condensed (2310) in IV and sent to the solvent cleaning (2300), and, in the second step, the crude isocyanate thus prepurified is freed of residual solvent and phosgene apart from traces and pumped into the purifying distillation (V) as stream 100. Step (III) was outlined here in a two-stage configuration; in the drawings, for the sake of simplicity, step (III) is shown as a one-stage distillation, which is also possible in principle given appropriate configuration.

As soon as the condensed solvent with traces of phosgene and crude isocyanate from (III) is pumped into the solvent cleaning (IV) comprising a pump receiver, a separating column with a vacuum system, a heat exchanger for preheating, a heat exchanger for vapor generation, a heat exchanger for condensing the vapors and a heat exchanger for cooling the solvent, the solvent with traces of phosgene and crude isocyanate is freed of phosgene. The vapors (130) thus formed, comprising phosgene and solvent, are conducted into the phosgene absorption (VI), and the solvent (120) thus purified is then pumped into the solvent tank (1040), where it is available for the supply of the amine pathway in the reaction zone (I).

As soon as the crude isocyanate from (III) which has been freed of residual solvent and phosgene apart from traces is pumped into the purifying distillation (V) comprising a distillation column 2400 with a vacuum system and separating apparatus, a heat exchanger for evaporation, a pump receiver and a heat exchanger for condensation, and optionally an upstream distillation column 2410 with a vacuum system and separating apparatus, a heat exchanger for evaporating, a pump receiver and a heat exchanger for condensation, for the optional removal of polymeric isocyanate fractions, the crude isocyanate 100 is freed of traces of solvent and, in the case of MDI, from phenyl isocyanate and other by-products, for example in the case of TDI from unwanted oligomers and polymers, and separated into the desired isomers. In this way, the desired isocyanate 1 is obtained in the desired purity and homolog and isomer distribution (streams 140 and 141).

The process offgas destruction system (VIII), comprising an activated carbon-filled apparatus operated under reduced pressure with a ventilator to a connected TAR, a pump receiver with pump and metering conduits, and a gas supply conduit, was in operation during the circulation mode as well and therefore need not be started up again.

The complete isocyanate production plant 10000 is now running with reduced load (startup load) and can now be run up to the desired target production. It is particularly preferable here to start up the production plant with reduced load, since the required temperature profiles for the phosgenation, the hydrogen chloride workup, the phosgene absorption and the various distillation units, for example owing to inadequate temperature profiles, are otherwise not available sufficiently quickly, which would lead to incomplete reactions, increased by-product formation and inadequate workup of the product.

The process of the invention gives rise to the following advantages:

i) Increase in productivity, because the availability of the plant increases, since the time taken for the running down and restarting of the plant for the production shutdown is greatly minimized ii) There are no capital costs for a greater plant capacity.

iii) There are no capital costs for a larger end product tank for buffering of prolonged shutdown times.

iv) Avoidance of superfluous waste products which arise in the event of incomplete reaction during the startup operation.

v) The cleaning of the solvent, for example the removal of phosgene and traces of isocyanates, promotes product quality and enables frictionless running of the reaction when the process is restarted.

vi) In many cases, energy is saved because there is no need for the preparations for the shut-down plant sections that are needed for the restart, such as the heating of the auxiliaries and feedstocks or the heating of the equipment etc.

vii) In many cases, there are savings of auxiliaries such as condensate and nitrogen.

viii) The susceptibility of pumps or compressors to need repair is reduced, since the bearings or seals thereof suffer from every restart when they are switched off in the event of a shutdown. Thus, subsequent repairs are avoided, which again has a positive effect on the productivity of the plant and maintenance costs.

The success of the procedure of the invention is surprising to the person skilled in the art because, in principle, in order to save energy and to be able to concentrate on the maintenance measures due in the production shutdown, the skilled person would be much more likely to shut down the entire plant, especially since additional capital costs for recycling pipelines including pumps, retrofitting in the apparatuses and additional process control technology have to be accepted for the process of the invention and for the plant of the invention. The present invention is to be illustrated hereinafter by further examples.

EXAMPLES

General Conditions for the Preparation of a Mixture of Methylene Diphenyl Diisocyanate and Polyethylene Polyphenylene Polyisocyanate (Collectively MDI Hereinafter) in Regular Operation—Cf. Also FIG. 1

4.3 t/h of a mixture of methylenediphenyldiamine and polymethylenepolyphenylenepolyamine (collectively MDA hereinafter; 2) at a temperature of 110° C. are mixed with 11 t/h of monochlorobenzene (MCB; 4) at a temperature of 30° C. as solvent by means of a static mixer (1020) to give a 28% MDA solution (20). Phosgene (3) is provided by means of a phosgene generator and a phosgene liquefier (IX). Thereafter, the phosgene (3) is diluted to a 35% phosgene solution (30) in a phosgene dissolution tank with stream (160) consisting predominantly of MCB (4). 24 tonnes per hour of 35% phosgene solution (30) at a temperature of 0° C. are reacted with 4.3 tonnes per hour of MDA (2) in the form of the 28% MDA solution (20) at a temperature of 45° C. in an adiabatic reaction, as described in EP 1 873 142 B1. After the two raw material solutions have been mixed in the mixing apparatus (1100), the reaction solution (50) obtained is run at a temperature of 85° C. through a suspension conduit into a heated phosgenation tower (1200). At the top of the phosgenation tower, the absolute pressure is 1.6 bar and the temperature is 111° C. The hydrogen chloride formed in the reaction is removed together with traces of phosgene and MCB as gas stream (70). The liquid reaction mixture (60) is withdrawn from the phosgenation tower (1200) and fed to the workup sequence (II ff.). For this purpose, it is first introduced as a sidestream into a heated dephosgenation column (II). At a top temperature of 116° C. and an absolute pressure of 1.6 bar, phosgene is removed overhead (90) together with traces of MCB and hydrogen chloride. Phosgene is absorbed in a phosgene absorption column (2500, VI) and run into the phosgene dissolution tank (1030), and hydrogen chloride is directed into a hydrogen chloride absorber 2600 (VII) and then into a hydrochloric acid tank 2610 for further use. After removal of hydrogen chloride and excess phosgene from the isocyanate-containing reaction solution (60), a crude isocyanate solution (80) is obtained, which is discharged from the bottom of the dephosgenation column 2100 and run at a temperature of 155° C. into a first distillation stage of the solvent distillation (III), in order to free it of the MCB solvent. The absolute pressure at the top of this solvent distillation column is 600 mbar at a bottom temperature of 145° C. MCB is drawn off in gaseous form overhead (110), and this MCB gas stream is condensed in an air condenser (2310). 2.5 t/h of this condensed solvent are sprayed into a scrubbing column (not shown in FIG. 1), in order to prevent any possible entrainment of isocyanate into the vacuum conduits. The remaining condensed MCB (20 t/h) is pumped to a solvent stripper 2300 in which the MCB is freed of phosgene, and the phosgene-containing vapors (130) are condensed and pumped into the phosgene absorber 2500, and the phosgene-free MCB from the bottom of the stripper (120) is pumped into the solvent tank (1040). The crude MDI (100) is discharged from the bottom of the column 2200 and freed of the residual MCB down to 1% in a second distillation column (not shown). The absolute pressure at the top of this solvent distillation column is 70 mbar at a bottom temperature of 150° C. MCB is drawn off in gaseous form overhead, and this MCB gas stream is condensed and recycled into the bottom of the first distillation column. Subsequently, in a countercurrent evaporator, at an absolute pressure of 20 mbar and a top temperature of 170° C., the product is freed of secondary components such as phenyl isocyanate and residual MCB. This affords 5.4 t/h of MDI as bottom product, which is worked up by means of further distillation steps (2410/2400) to give MDI of the desired purity (polymeric fractions 141/monomeric fractions 140) and then run into the corresponding MDI product tanks (2430/2440) for further use.

General Conditions for the Preparation of Phosgene in Regular Operation for Low-Temperature Combiners:

In a mixing tube, 810 m$^3$ (STP)/h of chlorine and 955 m$^3$ (STP)/h of carbon monoxide are mixed at 18° C. and a pressure of 1.8 bar (absolute). An excess of carbon monoxide is used relative to chlorine, such that, after the complete reaction of the chlorine, there is still 9% carbon monoxide remaining in the phosgene. The mixed gas composed of chlorine and carbon monoxide is run into a distributor present at the base of a shell and tube phosgene generator. There are 2 tonnes of activated carbon (Norit RB4C) present as catalyst in the tubes above the distributor. Over this catalyst, the mixed gas is depleted in a highly exothermic reaction to give phosgene. The reaction is cooled via water circulation by means of evaporative water cooling. The temperature of the phosgene in the exit line of the generator is 55° C. and the pressure is 1.53 bar (absolute). At this point, the completeness of the reaction is monitored by continuously measuring the residual chlorine content and the carbon monoxide content. The gaseous phosgene containing excess carbon monoxide which is prepared in this way is then condensed in a phosgene liquefier at −17° C. The bottom product from the phosgene liquefier runs into a phosgene dissolution tank (1030). Excess carbon monoxide does not condense and is run overhead into a downstream second phosgene generator of identical design, where it is contacted with an appropriate amount of chlorine, such that, after complete conversion of the chlorine, there is again still 9% of carbon monoxide remaining in the phosgene. Downstream of the second phosgene generator as well, the completeness of the reaction is monitored by continuously measuring the residual chlorine content and the carbon monoxide content. The phosgene thus prepared is condensed in a second phosgene liquefier at −17° C. The bottom product from the second phosgene liquefier likewise runs into the phosgene dissolution tank. As top product, excess carbon monoxide including traces of phosgene is guided into an offgas manifold, where it is freed of phosgene, and then combusted in a thermal waste air cleaning operation. Thus, 4.2 tonnes of phosgene per hour arrive in the phosgene dissolution tank.

In the phosgene dissolution tank 1030, the phosgene, if required, can be mixed with a solvent. For a production process for isocyanates, the phosgene in the phosgene dissolution tank is mixed with monochlorobenzene to give a 35% phosgene solution and withdrawn at −2° C. for further use. (In other industrial scale processes, phosgene can also be used in the form of pure liquid phosgene.)

Example 1 (Comparative Example)

Brief shutdown of the MDI plant with complete stoppage of the plant, repair measure and restarting of the MDI plant The brief shutdown of the plant served to change a defective heat exchanger in the phosgene liquefaction in the phosgene production. For this purpose, the MDI plant is run down completely, i.e. the reaction zone, dephosgenizer, solvent distillation, solvent cleaning, purifying distillation, hydrogen chloride absorption and process offgas destroyer. The energy supplies are switched off during the repair measure. After the measure, the plant is started up again, for which it was necessary to inertize, fill and heat the entire plant beforehand.

Procedure for the Complete Stoppage of the Plant:

The preparation of 5.4 t/h of MDI in continuous mode is conducted at nameplate load as described in the general conditions. The reaction zone is run down by first stopping the MDA supply. MCB from the MDA solution supply and the phosgene solution from the phosgene dissolution tank continue to run with the nameplate load volume set beforehand for one hour. Subsequently, the phosgene supply is stopped, and the reaction zone is freed of phosgene with a two-hour purge with solvent. The mixing unit cools down directly after stoppage of the MDA stream. The temperature of the phosgenation reactor is kept at 110° C. during this period by means of industrial heating. After the 2 hours, the heating is switched off and the phosgenation plant is allowed to cool down, in the course of which the phosgenation reactor filled with solvent is left to stand and the plant pressure adjusts correspondingly. The reaction zone is now out of operation. The shutdown of the phosgenation took a total of 3 h.

After stoppage of the MDA stream, the phosgene preparation is shut down immediately. As soon as residual MDA has been depleted by phosgenation reaction, the phosgene preparation has to be shut down since only a small storage capacity for phosgene is available because it is desirable to keep the phosgene stock in the plant as low as possible. No later than after 15 minutes, therefore, the phosgene generators have to be shut down. When running down this plant, the second phosgene generator is first shut down by stopping the chlorine supply, while the carbon monoxide stream is allowed to continue and is conducted to the offgas supply of the TAR. Once the chlorine supply in the second phosgene generator has been closed, the supply of chlorine and carbon monoxide to the first phosgene generator is simultaneously throttled. The amount of the two feedstocks that are introduced into the mixing tube during the rundown time of 15 minutes is lowered constantly from 545 m$^3$ (STP)/h to 0 m$^3$ (STP)/h of carbon monoxide and constantly from 455 m$^3$ (STP)/h to 0 m$^3$ (STP)/h of chlorine. The temperature in the mixing tube is still 18° C. and the pressure falls immediately from 1.8 to 1.2 bar absolute. The exothermic reaction to give phosgene in the phosgene generators is immediately ended.

The heat of reaction abates and the water circulation of the evaporative water cooling shuts down automatically. After 10 minutes, temperature in the exit line from the generator falls from 55° C. to 18° C. and the pressure falls from 1.53 bar to 1.2 bar absolute. The phosgene condensation in the shell and tube heat exchange of the phosgene liquefier that follows the phosgene preparation shuts down automatically and the cooling of the shell and tube heat exchanger is closed at one end, with warming of the heat exchanger from −17° C. to 18° C. In the phosgene dissolution tank downstream thereof, the 35% phosgene solution is diluted because there is no further freshly prepared phosgene coming in and the phosgene dissolution tank is now being filled only from the phosgene absorption with a mixture of phosgene and monochlorobenzene. The phosgene preparation has now been shut down. The plant inlets and plant outlets are closed, the mixing tube is under carbon monoxide and chlorine, and there is phosgene in the phosgene generators. The shutdown of the phosgene preparation took a total of 15 minutes.

During the three-hour shutdown of the reaction zone, the liquid phase thereof continues to run through the dephosgenizer, the liquid phase of which runs to the solvent distillation and the gaseous phase of which is switched to the phosgene absorption. During the three-hour purge, the dephosgenizer is heated to 130 bar with 15 bar steam. After the purging operation, the steam to the dephosgenizer is closed, and the dephosgenation is at rest and cools down. The vapor pathway to the phosgene absorber remains open. If no MCB solvent is present any longer in the bottom of the dephosgenizer, the discharge pump to the solvent distillation is shut down. The dephosgenation is at rest about 5 minutes after the reaction zone.

During the three-hour shutdown of the reaction zone, the liquid phase thereof continues to run through the dephosgenizer and thence into the solvent distillation. During the three-hour purge, operation of the solvent distillation continues. The crude isocyanate solution which is discharged from the bottom of the dephosgenation column and is run into the first distillation stage at a temperature of 155° C. is diluted over the 3 h until only MCB solvent is arriving. The absolute pressure at the top of this solvent distillation column changes with increasing crude MDI concentration from 600 mbar to 800 mbar, and the bottom temperature falls from 150° C. to 120° C. MCB is drawn off in gaseous form overhead and condensed in an air cooler. 2.5 t/h of this condensed solvent are sprayed into a scrubbing column, in order initially to prevent any possible entrainment of isocyanate into the condensation system. The falling amounts of residual condensed solvent are pumped via a receiver by means of a discharge pump into the solvent cleaning operation. The liquid phase with a vanishingly small crude MDI content is discharged from the bottom of the column and run into the second distillation column, in order to purge it. The absolute pressure at the top of this solvent distillation column is 200 mbar at a bottom temperature of 110° C. MCB is drawn off in gaseous form overhead, and this MCB gas stream is condensed and recycled into the bottom of the first distillation column. The bottoms from the second distillation column are pumped at low temperature to the purifying distillation via a countercurrent evaporator, the heating of which is switched off in the absence of crude MDI about 30 minutes after stoppage of the MDA stream into the reaction zone. The solvent distillation is at rest 2 hours after the purging in the reaction zone has ended.

During the three-hour purging of the reaction zone, the liquid phase thereof continues to run through the dephosgenizer, through the solvent distillation and thence into the purifying distillation. During the three-hour purge, operation of the purifying distillation continues. The crude isocyanate solution which is discharged from the bottom of the solvent distillation and run into the first stage of the purifying distillation at a temperature of 120° C. is diluted by MCB solvent after only 30 minutes to such an extent that the heating of the purifying distillation has to be switched off. The absolute pressure at the top of this purifying distillation changes with decreasing crude MDI concentration from 6 mbar to 200 mbar, and the bottom temperature falls from 220° C. to 100° C. With the adjustment of the heating, the distillation has ended and the bottoms from the purifying distillation are pumped into an MDI product tank. The purifying distillation is shut down together with the solvent distillation.

During the three-hour purging of the reaction zone, the liquid phase thereof continues to run through the dephosgenizer, through the solvent distillation and thence into the purifying distillation. During the three-hour purge, operation of the solvent cleaning continues. With the shutdown of the solvent distillation, there is no further solvent condensing out of the gas phase from the solvent distillation. The intake via a reservoir by means of a discharge pump into the solvent cleaning is closed, the discharge pump is switched off, and the circulation pump of the solvent cleaning is switched off and the heating of the evaporator of the solvent cleaning is closed.

As long as there are still vapors arising from the reaction zone, the dephosgenizer and the condensed vapors from the solvent cleaning, the phosgene absorption also continues to run. After the shutdown of the reaction zone, the dephosgenizer and the solvent cleaning, the phosgene absorption can also be run down. The intake of the gaseous phase from the reaction zone and the dephosgenizer into the phosgene absorber remains open. As soon as the solvent cleaning is in operation, the distillate therefrom runs into the phosgene absorber. The path of the offgas from the phosgene absorber to the hydrogen chloride absorption thus remains open for as long as the process offgas destruction plant is running. The pressure of the phosgene absorber remains constant at 1.6 bar absolute over the entire shutdown phase, and the temperature remains constant at 0° C. The MCB (−17° C.) which is applied to the top of the phosgene absorption for scrubbing of the offgas is shut down. The cooling of the phosgene absorption is shut down 1 hour after the shutdown of the solvent cleaning. The phosgene absorption is then at rest and warms up to ambient temperature.

For as long as the phosgene absorption is in operation, the hydrogen chloride absorption remains in operation. The hydrogen chloride-containing gas phase from the reaction zone and the dephosgenizer which enter the phosgene absorber and thence the hydrogen chloride absorption rapidly loses hydrogen chloride. The hydrogen chloride gas in the gaseous phase from the phosgene absorption is absorbed in an absorption apparatus with acidic water from the process offgas destruction and additional condensate water in an exothermic reaction to give hydrochloric acid and run into the hydrochloric acid tank. The offgas still goes to the process offgas destruction. Within 30 minutes, the amount of hydrogen chloride arriving falls to such a degree that only weak hydrochloric acid is being formed, which is switched into a weak hydrochloric acid tank provided for the purpose. At the same time, the amounts of condensate are throttled significantly from 3.2 t/h to 1 t/h and weak acid from 5.4 t/h to 3 t/h to the hydrogen chloride absorption. As soon as the phosgene absorption has been shut down, the application of condensate and weak acid to the hydrogen chloride absorber is stopped. The pathway to the hydrochloric acid tank is closed. The pathway to the weak hydrochloric acid tank remains open. The pathway from phosgene absorber via hydrogen chloride absorption and including the process offgas destruction remains open. The hydrogen chloride absorption is at rest 30 minutes after the phosgene absorber.

Then the vacuum system is shut down by switching off the vacuum pumps for the solvent distillation and the solvent cleaning and also the purifying distillation. The plant sections are vented to standard pressure with nitrogen. These operations take 1 hour.

Downstream of the vacuum system, the refrigeration system (ammonia refrigeration system) with which MCB is cooled to −17° C., in order to operate the phosgene absorber, the phosgene liquefier and vacuum system, is switched off. This operation takes 30 minutes.

Then the process offgas destruction system is shut down by first closing the offgas pathway from the phosgene absorption to the hydrogen chloride absorption and then that from the hydrogen chloride absorption to the process offgas destruction. The application of water to the activated carbon-filled apparatus operated at a reduced pressure of 980 mbar absolute is stopped. The ventilator is switched off. The water circulation comprising pump and pump receiver is shut down. These operations take 1 hour.

Lastly, the thermal offgas cleaning is put out of operation by closing the process offgas pathway, stopping the natural gas flame, shutting down the scrubber circuit of the flue gas scrubbing, and, at the end, switching off the offgas ventilator. This operation takes 30 minutes.

Now the entire MDI plant is at rest. The plant pressure is set to ambient pressure. The residual emptying valves of all plant sections are opened in order to discharge residual substances from the plant. The complete shutdown with emptying and purging of all apparatuses, pumps and pipelines took a total of 24 hours. The plant component of the phosgene preparation is, as described below, prepared for the maintenance measure.

Procedure for the Maintenance Measure

It was necessary to replace a defective heat exchanger in the phosgene liquefier. As described above, the phosgene generation is at rest 15 minutes after the amine supply to the reaction zone has been closed. The phosgene condensation in the shell and tube heat exchanger of the phosgene liquefier which follows downstream of the phosgene preparation shuts down automatically, as described above. Once the MDI plant is at rest, the shell and tube heat exchanger is closed on the product side at the inlet and outlet. MCB solvent is connected and the apparatus is purged therewith for 3 h. Subsequently, the MCB is blown out with nitrogen for 2 hours. The shell and tube heat exchanger is also closed at the same time at the inlet and outlet on the coolant side. The MCB coolant is blown clear with nitrogen. Then this shell and tube heat exchanger is changed. After incorporation of the replacement shell and tube heat exchanger, the system is tested for leaks with nitrogen. The time required for this purpose is 8 hours.

The changing of the defective heat exchanger took a total of 13 hours and the overall plant is ready for operation again after 37 hours. In modern automated production plants, an important role is played by the number of personnel required for the preparation for the changing of the heat exchanger, namely partial emptying of the plant, mounting of the purging conduits for cleaning of the defective heat exchanger with inlet and outlet. In this case, one additional production worker is required. Workmen for the disassembly and assembly of the pipelines and for the change of heat exchanger are likewise required.

Procedure for the Restarting of the MDI Plant:

After the 13-hour repair operation on the phosgene liquefier, the phosgene preparation, once the system has been found to be free of leaks with nitrogen and the valves on the product and coolant side of the shell and tube heat exchanger have been opened, is ready for startup of the plant. Now the restart of the MDI plant can commence with the gradual commissioning of the individual plant sections.

Startup of the Process Offgas Destruction Plant:

First of all, the thermal offgas cleaning (TAR) is put into operation by switching on the offgas ventilator and then the scrubber circuit of the flue gas scrubbing, then lighting the natural gas flame and, lastly, opening the process offgas pathway. These operations take 16 hours.

Then the process offgas destruction system is started up by first switching on the water circuit comprising pump and pump receiver and the ventilator. Then the application of water to the activated carbon-filled apparatus operated at a reduced pressure of 980 mbar absolute is commenced. Finally, the offgas pathways from the hydrogen chloride absorption to the process offgas destruction and from the phosgene absorption to the hydrogen chloride absorption are opened. These operations take 2 hours.

Startup of the Cooling Systems and Auxiliary Systems:

The circuits of the auxiliary solvent systems are first put into operation by starting up the circulation pumps that control the temperature of the various heat exchangers of the 3 auxiliary solvent systems having different temperatures (cold: −17° C., cool: 20° C. to 30° C., warm: 50° C.). Then the refrigerator system (ammonia refrigerator system) with which MCB is cooled to −17° C., in order to operate the heat exchangers of the phosgene absorber, the phosgene liquefier, the solvent distillation and the vacuum system, is started up. At the end, the vacuum generation is put into operation by switching on the vacuum pumps. These operations take 4 hours.

Startup of the Solvent Distillation:

The distillation columns are filled with MCB solvent up to the 50% level and the pumping of MCB in circulation through the evaporator by means of circulation pumps is put into operation. The vacuum pathway is opened and the evaporator is heated. The absolute pressure at the top of the first solvent distillation column reaches 800 mbar absolute and a bottom temperature of 123° C. is established, with commencement of distillation of the solvent. MCB is drawn off in gaseous form overhead and condensed in an air cooler. 2.5 t/h of this condensed solvent are sprayed into a scrubbing column, in order to prevent possible entrainment of isocyanate into the condensation system at a later stage. The residual condensed amounts of solvent run into the reservoir for the solvent cleaning. The liquid phase from the first distillation column is discharged from the bottom of the column and run into the second distillation column. The vacuum pathway is opened and the evaporator is heated. The absolute pressure at the top of this solvent distillation column reaches 80 mbar absolute and a bottom temperature of 60° C., at which the MCB solvent starts to boil. MCB is drawn off in gaseous form overhead, and this MCB gas stream is condensed and recycled into the bottom of the first distillation column. For further commissioning of the solvent distillation, the solvent cleaning has to be started up. As soon as this has been started up, solvent runs into the solvent tank. From the tank, the solvent is run via the reaction zone and the dephosgenizer into the solvent distillation, with startup of the heating of the reaction zone and the dephosgenizer. Then the solvent distillation is ready for operation and runs in a circuit via the solvent cleaning, the solvent tank, the reaction zone and the dephosgenizer. This operation takes 8 hours. As soon as the phosgenation in the reaction zone is started, crude MDI is formed, which arrives in the solvent distillation via the dephosgenizer. When the crude MDI arrives, the MCB solvent is removed as vapor overhead and the crude MDI that has been freed of the majority of solvent from the bottoms of the solvent distillation is pumped to the purifying distillation. The absolute pressure at the top of the first solvent distillation column is set at 500 mbar and a bottom temperature of 145° C. is established by closed-loop control. The absolute pressure at the top of the second solvent distillation column is set at 70 mbar by closed-loop control and a bottom temperature of 150° C. is established.

Startup of the Solvent Cleaning:

The startup of the solvent distillation gives rise to solvent condensing out of the gas phase from the solvent distillation. The vacuum pathway is opened. The intake via the reservoir by means of the discharge pump that has been put into operation into the solvent cleaning is opened. The circulation pump of the solvent cleaning is started up and the heating of the evaporator of the solvent cleaning is opened. At an absolute pressure of 500 mbar and a temperature of 107° C., vapors are generated that are supplied in condensed form to the phosgene absorption, which means that the phosgene absorption has started by virtue of these condensed vapors being applied to the scrubbing column thereof, but has not yet been run up. The phosgene-free bottoms from the solvent cleaning are pumped into the solvent tank. These operations take 4 hours.

Startup of the Phosgene Absorption:

As soon as the condensed vapors from the solvent cleaning arrive, the valves of the auxiliary solvent systems (cool and cold) are opened in order to be prepared for the hot vapors that arise on startup of the reaction zone. The cold MCB which is applied to the top of the phosgene absorption for scrubbing of the offgas is started up. The output from the phosgene absorption is switched to the phosgene dissolution tank. Subsequently, the pathway from the phosgene dissolution tank to the reaction zone is opened. The phosgene absorption is now ready to also accept the vapors from the reaction zone and the dephosgenizer. With the start of the phosgenation, hydrogen chloride arrives, which is conducted onward via the open offgas pathway to the hydrogen chloride absorption. The excess phosgene is condensed and scrubbed out and runs off with the condensed solvent to the phosgene dissolution tank. The pressure of the phosgene absorber remains constant at 1.6 bar absolute over the entire startup phase, and the temperature is lowered to 0° C.

Startup of the Phosgene Preparation:

The phosgene plant is started up by running carbon monoxide and chlorine into the carbon monoxide- and chlorine-filled mixing tube with a time delay of 1 minute. The amount of the two feedstocks that are introduced into the mixing tube during the startup time t of 45 minutes, and for chlorine correspondingly only 44 minutes, is raised constantly from 0 m$^3$ (STP)/h to 545 m$^3$ (STP)/h of carbon monoxide and constantly from 0 m$^3$ (STP)/h to 455 m$^3$ (STP)/h of chlorine. After 45 minutes, a carbon monoxide content in the phosgene of 9% is found. The temperature in the mixing tube is 18° C. and the pressure is adjusted immediately to 1.8 bar absolute. Carbon monoxide and, with a time delay, the mixed gas composed of chlorine and carbon monoxide enter the interior of the shell and tube phosgene generator which is at 18° C. The reaction to give phosgene starts up immediately and is highly exothermic. The heat of reaction is removed via water circulation by means of evaporative water cooling. The temperature of the phosgene in the exit line of the generator after 5 minutes is 55° C. and the pressure is 1.57 bar absolute. The phosgene thus prepared, as described in the general preparation conditions, is condensed in the phosgene liquefier and collected in the phosgene dissolution tank. The phosgene liquefier is ready for operation when the heat exchangers have been cooled with MCB at −17° C. and the offgas stream of the liquefier is being washed with MCB at −17° C. After 45 minutes, these flow rates are increased to a reactant flow rate of 810 m$^3$ (STP)/h of chlorine and 955 m$^3$ (STP)/h of carbon monoxide. The phosgene preparation is now running, and the phosgene concentration in the phosgene dissolution tank is gradually concentrated to a 35% phosgene solution within 6 hours.

Start of the Phosgenation in the Reaction Zone:

The phosgenation tower is filled with solvent up to the height of the overflow and, with the aid of a heat carrier, the phosgenation tower has already been heated up to 105° C. As soon as the phosgene solution concentration reaches 25 percent, the amine pathway to the reaction zone is opened. The amine concentration is 18 percent. During the startup, a stoichiometric excess of phosgene relative to MDA of 140 percent is established. The reaction zone is put into operation with a load of 15% of the nameplate load. As well as crude MDI, the reaction also immediately forms hydrogen chloride which, together with excess phosgene and a proportion of the solvent, takes the gas pathway to the phosgene absorber. After one hour, the MDA solution supply is increased to a load of 25% of the nameplate load, which corresponds to a production output of 1.35 t/h (MDI). The two flow rates are only increased to the nameplate load of 5.4 t/h of MDI when the purifying distillation discharges on-spec end product into the production tank. This operation takes 12 hours. When the reaction zone is running at nameplate load, a stoichiometric phosgene to MDA excess of 100 percent is established. The MDA concentration in solvent is then adjusted to 28 percent. The phosgene concentration in the phosgene solution has now reached 35 percent.

Startup of the Dephosgenizer:

The dephosgenizer is in circulation with MCB solvent from the solvent tank, via the reaction zone to the solvent distillation and solvent cleaning. As soon as the first crude MDI, solvent and phosgene arrives from the overflow of the phosgenation tower of the reaction zone, the phosgenation tower is run up to a target temperature of 157° C. in the dephosgenation bottoms at 1.6 bar absolute and is thus in operation. The vapor pathway to the phosgene absorber was open the whole time. Phosgene and traces of solvent leave the dephosgenizer via the gas pathway, and dephosgenized crude MDI is pumped to the solvent distillation.

Startup of the Hydrogen Chloride Absorption:

The offgas pathways coming from the phosgene absorber and going to the process offgas destruction are open. First, the application of condensate and weak acid to the hydrogen chloride absorber is started up. The pathway to the hydrochloric acid tank is closed. The pathway to the weak hydrochloric acid tank remains open. As soon as the first hydrogen chloride after the start of the phosgenation finds its way through the phosgene absorber into the hydrogen chloride absorption, by closed-loop control of condensate and weak hydrochloric acid from the weak hydrochloric acid tank, the hydrochloric acid concentration in the output from the hydrogen chloride absorber is adjusted to 31 percent.

The pathway of the hydrochloric acid to the hydrochloric acid tank is opened and the pathway to the weak hydrochloric acid tank is closed. Now the hydrogen chloride absorption is in operation. This operation takes 2 hours and runs in parallel with the commissioning of the phosgenation.

Startup of the Purifying Distillation:

As soon as the absolute pressure at the top of the second solvent distillation column has been set by closed-loop control at 70 mbar and a bottom temperature of 120° C. has been attained, the bottoms from this second solvent distillation column are switched to the intake of the purifying distillation. At a level of 60 percent in the first column of the purifying distillation, the circulation pump is put into operation and the crude MDI is heated further by means of the evaporator. At a reduced pressure of 6 bar absolute and a bottom temperature of 220° C., the crude isocyanate is freed of traces of solvent and of phenyl isocyanate. The bottoms from the first column of the purifying distillation are run into the second column of the purifying distillation. Here too, the circulation pump is put into operation and the crude MDI is heated further by means of the evaporator. In the second column, at 6 mbar absolute and a bottom temperature of 220° C., the monomeric MDI is separated via the top of the column from the polymeric MDI, which is drawn off in the column bottoms. The polymeric bottom product is pumped into an MDI product tank. The monomeric MDI obtained at the top of the column is separated into the desired composition of the isomers in further columns, in order then to be run into the respective product tanks.

The MDI plant is now running at 25% of the nameplate load. The running of the production plant up to nameplate load, which is automated in a modern production plant, takes another 6 hours. It is absolutely necessary to start up the production plant at reduced load, since the temperature profiles required for the phosgenation reaction, the solvent distillation, the solvent cleaning and the purifying distillation are otherwise not available quickly enough. This would lead to incomplete reactions, increased by-products and inadequate workup of the product. Moreover, in terms of time, it is important to start up the plant component of the phosgene preparation in such a way that phosgene is available when the phosgenation reaction is to be started. When said phosgene preparation also supplies other users, the production load of this plant then merely has to be run up in good time.

Assessment of the Energy and Auxiliaries Required and Time Taken for the Running Down and Starting Up of the Plant Including the Cleaning Measure:

The total time taken for the measure was 81 hours. This applies if sufficient personnel is available and no technical difficulties occur. The time taken for the repair measure itself was 13 hours. For the shutdown, 24 hours were required. The startup took a further 44 hours.

Thus, a total of 437.4 tonnes of MDI production was lost.

Example 2 (Inventive)

Brief shutdown of the MDI plant with circulation mode in the plant sections unaffected by the repair measure, repair measure and restarting of the MDI plant The brief shutdown of the plant served to change a defective heat exchanger in the phosgene liquefaction in the phosgene production. For this purpose, the phosgene production is run down completely and the other plant sections such as reaction zone, dephosgenizer, solvent distillation, solvent cleaning, purifying distillation, hydrogen chloride absorption and process offgas destroyer are put into circulation mode. During the repair operations, the energy sources are switched off only in the region of the phosgene production. The vacuum system remains in operation. After the repair operations, the plant is started up again, wherein it is necessary merely to inertize the heat exchanger that has been changed in the phosgene preparation and fill it with cooling medium.

Procedure for the Complete Stoppage of the Phosgene Preparation and Adjustment of the Remaining Plant Sections of the MDI Plant to Circulation Mode:

The phosgene preparation is shut down as described in example 1. At the same time, the adjustment of the MDI plant to circulation mode commences with the shutdown of the input stream of MDA into the mixing unit of the reaction zone. For this purpose, the MDA supply to the reaction zone is stopped and the MDA pathway from the MDA reservoir tank is purged with MCB for 10 minutes to free it of MDA. The reaction zone of the phosgenation plant is purged with phosgene solution, with depletion of MDA still present in the phosgenation tower by reaction to give crude MDI. This dilutes the crude MDI solution. The heat of reaction abates after stoppage of the MDA supply. The temperature of the phosgenation reactor is kept at 110° C. by means of industrial heating. Phosgene solution from the phosgene dissolution tank which, as stated, is being ever further diluted is run through the reaction zone and the circulation mode is established via the dephosgenizer, the phosgene absorber and the phosgene dissolution tank back to the mixer in the reaction zone. The pressure in the reaction zone remains at 1.4 bar (absolute) during the circulation mode.

As soon as the phosgenation in the reaction zone has ended with the stopping of the MDA supply, the dephosgenizer, as described above, is put into circulation mode with the reaction zone and the phosgene absorber. During the circulation mode, the liquid phase from the reaction zone continues to run through the dephosgenizer, the liquid phase of which runs to the solvent distillation and the gaseous phase of which is switched to the phosgene absorption. For this purpose, the dephosgenizer continues to be heated with steam, keeping the bottom temperature at 150° C. The concentration of crude MDI in the dephosgenizer decreases.

As soon as the phosgenation in the reaction zone has ended with the stopping of the MDA supply, the phosgene absorber, as described above, is put into circulation mode with the reaction zone and the dephosgenizer. The intake of the gaseous phase from the reaction zone and the dephosgenizer into the phosgene absorber remains open. Since the solvent cleaning is also still in operation, the distillate therefrom likewise runs into the phosgene absorber. The path of the offgas from the phosgene absorber to the hydrogen chloride absorption likewise remains open. The pressure of the phosgene absorber remains constant at 1.6 bar absolute over the entire circulation mode, and the temperature remains constant at 0° C. The MCB (−17° C.) which is applied to the top of the phosgene absorption for scrubbing of the offgas is reduced from 15 tonnes per hour to 4 tonnes per hour. The cooling of the phosgene absorption is kept in operation.

Thus, with the shutdown of the MDA supply to the mixing unit, a first circulation mode of the reaction zone, in gaseous form from the phosgenation tower into the phosgene absorber and in liquid form from the phosgenation tower to the dephosgenizer and in gaseous form from the dephosgenizer to the phosgene absorption and thence in liquid form via the phosgene dissolution tank back to the mixer in the reaction zone of the MDI plant is established.

A second circulation mode is established after shutdown of the MDA supply into the mixing unit in the reaction zone from the intake of the bottoms from the dephosgenizer into the solvent distillation, via the solvent cleaning, the solvent tank and via the reaction zone back to the dephosgenizer.

The solvent distillation is still heated in circulation mode. The crude isocyanate solution which is discharged from the bottom of the dephosgenation column and is run into the first distillation stage at a temperature of 150° C. is diluted during the circulation mode until only MCB solvent is arriving. The absolute pressure at the top of this solvent distillation column changes with increasing crude MDI concentration from 600 mbar to 800 mbar, and the bottom temperature falls from 150° C. to 120° C. MCB is drawn off in gaseous form overhead and condensed in an air cooler. 2.5 t/h of this condensed solvent are sprayed into a scrubbing column, in order initially to prevent any possible entrainment of isocyanate into the condensation system. The falling amounts of residual condensed solvent are pumped via a receiver by means of a discharge pump into the solvent cleaning operation. The liquid phase with a vanishingly small crude MDI content is discharged from the bottom of the column and run into the second distillation column. The absolute pressure at the top of this second solvent distillation column is 200 mbar at a bottom temperature of 110° C. MCB is drawn off in gaseous form overhead, and this MCB gas stream is condensed and recycled into the bottom of the first distillation column. The bottoms from the second solvent distillation column are still discharged during circulation mode.

The solvent cleaning is still heated in circulation mode. From the solvent distillation, there is still no solvent condensing out of the gas phase from the solvent distillation. The intake via a reservoir by means of a discharge pump into the solvent cleaning remains open, the discharge pump and the circulation pump of the solvent cleaning remain in operation, and the heating of the evaporator of the solvent cleaning is maintained. As soon as the solvent cleaning is in operation, the distillate therefrom runs into the phosgene absorber. The bottoms from the solvent cleaning, consisting of inert MCB solvent, are condensed and run into the solvent tank.

This second circulation mode is put into operation by running the solvent from the solvent tank to the reaction zone and thence into the dephosgenizer and thence back into the intake of the solvent distillation.

Thus, with the shutdown of the MDA supply to the mixing unit, a second circulation mode of the reaction zone, in liquid form from the phosgenation tower into the dephosgenizer and in liquid form from the dephosgenizer into the solvent distillation and thence in gaseous form overhead, then in condensed form, into the solvent cleaning, thence from the liquid phase into the solvent tank and thence back to the mixer in the reaction zone of the MDI plant is established.

A third circulation mode is established with the bottoms from the second distillation column of the solvent distillation. For this purpose, these bottoms are pumped as input at low temperature to the polymer removal (2410) via a countercurrent evaporator, the heating of which is switched off in the absence of crude MDI about 30 minutes after stoppage of the MDA stream into the reaction zone. The heating of the purifying distillation is likewise shut down. The bottoms from the purifying distillation, consisting mainly of a mixture of MCB solvent and crude MDI, are pumped into a crude MDI storage tank (not shown). From the crude MDI storage tank, the MCB solvent containing a low level of MDI is pumped back into the intake of the first distillation column (2200) of the solvent distillation. Thus, the third circulation mode is established.

The offgas pathway proceeding from the gaseous phase of the phosgene absorber into the hydrogen chloride absorption and thence via the gaseous phase into the process offgas destruction including TAR is open. A fourth circulation mode is established by switching the output from the hydrogen chloride absorption from the hydrochloric acid tank to the weak hydrochloric acid tank. Thence, the weak hydrochloric acid is returned to the top of the absorber for the hydrogen chloride absorption.

The last remaining plant component of process offgas destruction need not be switched to circulation mode since the normal operation thereof is already a circulation mode. The process offgas pathway, as described above, proceeding from the gaseous phase of the phosgene absorber into the hydrogen chloride absorption and thence via the gaseous phase into the process offgas destruction including TAR is open. Normal operation means firstly that the thermal exhaust gas cleaning (TAR) is in operation, the offgas ventilator and the scrubber circuit of the flue gas scrubbing are running and the natural gas flame is ignited, and secondly that the process offgas destruction system is in operation, the water circuit comprising pump and pump receiver and the ventilator are running, and the application of water to the activated carbon-filled apparatus being operated at a reduced pressure of 980 mbar absolute is running The only difference from normal operation is that the weak hydrochloric acid tank, which is filled up as a result of the continuous application of water to the activated carbon-filled apparatus for process offgas destruction and the output thereof to the weak hydrochloric acid tank, is discharged to the water treatment plant.

The entire MDI plant, apart from the phosgene preparation that has been shut down, is now running in circulation mode. The preparation (establishment of circulation mode of reaction zone, dephosgenizer, solvent distillation, solvent cleaning, purifying distillation, hydrogen chloride absorption and process offgas destroyer, and the shutdown of the phosgene preparation) for the repair measure, not including purging and emptying of the apparatuses, pumps and pipelines, took a total of 15 minutes.

Procedure for the Repair Measure:

the repair measure was conducted as described in example 1.

Preparation for Restarting of the Plant

The preparations for restarting the plant were minimal, since almost all plant sections are already in circulation mode. It is merely necessary to prepare the phosgene preparation after the repair, as described in example 1, and then put it into operation.

Restarting of the Plant

Once the phosgene preparation is in operation, phosgene arrives in the phosgene dissolution tank of the reaction zone. As soon as the phosgene solution concentration reaches 25 percent, which is the case after 45 minutes, the amine pathway to the reaction zone is opened and the phosgenation is started up as described in example 1. The startup of the other plant components is likewise conducted from circulation mode as described in example 1 (comparative example). The discharge of the output from the weak hydrochloric acid tank to the water treatment plant is ended and switched to the top of the absorber of the hydrogen chloride absorption as soon as the first hydrochloric acid is formed from hydrogen chloride in the hydrogen chloride absorption. As soon as fresh crude MDI is obtained in the bottom of the column 2410 (polymer removal), the heating of the column is put into operation, and as soon as the bottoms have been freed of solvent, the bottoms from the crude PMDI storage tank (2420 in FIG. 5) are switched to the MDI storage tank 2430. During circulation mode, the column (2400) was no longer fed via the distillate withdrawal from column (2410), but continued to run in the manner of a distillation from a storage tank (not shown). When fresh MMDI (distillate withdrawal from the column 2410) arrives in the column (2400) on restart, the distillation is run back up to target load.

As described in example 1, the MDI plant is now running at 25% of nameplate load. The running of the production plant up to nameplate load, which is automated in a modern production plant, then likewise takes another 2 hours.

The time taken for the entire operation (running down, execution of the measure and startup) was 16 hours. The time taken for the repair measure itself was 13 hours. For the shutdown, 15 min were required. The startup took 2 hours and 45 min.

Thus, a total of 86.4 tonnes of MDI production was lost.

Thus, given a nameplate load of 129.6 tonnes per day, there was extra production of 351 tonnes of MDI compared to example 1 (comparative example).

CONCLUSION in inventive example 2 with circulation mode, in percentage terms, 64% less primary energy (steam and power) and 80% less nitrogen are consumed than in the case of a complete shutdown of the plant as in example 1 (comparative example). In addition, greatly improved productivity of the plant is found, since more than 300 tonnes more of MDI were producible because of the shorter time taken for the whole operation (running down, measure and startup).

The invention claimed is:

1. A process for preparing isocyanates, comprising:
  I) reacting an amine with phosgene in the liquid phase in a reaction zone comprising
    I.1) a unit for providing an amine in the form of an amine solution in a solvent,
    I.2) a unit for providing phosgene in the form of a phosgene solution in a solvent,
    I.3) a unit for providing a solvent,
    I.4) a mixing unit for mixing the amine solution in the solvent with the phosgene solution in the solvent and optionally further solvent, the mixing unit being configured to be continuously charged with the amine solution in the solvent, the phosgene solution in the solvent, and optionally further solvent, and
    I.5) a reaction space arranged downstream of the mixing unit, for conducting a phosgenation reaction, with a separator unit optionally connected downstream, wherein the reaction space and/or the separator unit have outlet conduits for a liquid stream and a gaseous stream;
  wherein
    the amine, in the form of the amine solution with a mass flow rate $m_2$ from the unit for providing an amine, and
    the phosgene, in the form of the phosgene solution with a mass flow rate $m_3$ from the unit for providing phosgene, and optionally solvent from the unit for providing a solvent with a mass flow rate $m_4$ are conducted into the mixing unit and mixed therein, and
    the mixture obtained is converted in the downstream reaction space and separated into a liquid stream comprising crude isocyanate and solvent, and a gaseous stream comprising phosgene and hydrogen chloride;

II) separating the liquid stream from step I) into a liquid stream comprising solvent and crude isocyanate, and a gaseous stream comprising phosgene and hydrogen chloride in a distillation apparatus;

III) separating the liquid stream obtained in II) into a gaseous stream comprising solvent and a liquid stream comprising crude isocyanate in a distillation apparatus;

IV) separating the gaseous stream obtained in III), into a liquid stream comprising solvent and a gaseous stream comprising phosgene in a distillation apparatus;

V) obtaining a liquid isocyanate stream from the liquid stream obtained in III), resulting in a gaseous stream comprising secondary components and optionally solvent, in a distillation apparatus, and which optionally comprises removing polymeric isocyanate fractions in an upstream unit for polymer removal as a separate stream;

VI) absorbing the gaseous streams obtained in steps I), II) and IV) in solvent to obtain a liquid stream comprising solvent and phosgene, and a gaseous stream comprising hydrogen chloride in an absorption apparatus;

VII) optionally, absorbing the gaseous stream obtained in VI) in water or dilute hydrochloric acid in an absorption apparatus with formation of an offgas stream;

VIII) optionally, cleaning offgas streams at least from VII), in a workup apparatus configured to work-up offgas obtained from at least step VII);

IX) optionally, preparing phosgene from carbon monoxide and chlorine in an apparatus configured to prepare phosgene, and which is connected to the unit for provision of phosgene;

wherein
the process is interrupted, the interruption comprising shutting down one or more, but not all, plant sections from (I) to (IX), reducing the mass flow rate $m_2$ to zero and, in at least one of the plant sections that has not been shut down,
(i) recycling the output stream from this at least one plant section which has not been shut down into the respective plant section,
or
(ii) conducting the output stream from this at least one plant section which has not been shut down into a plant section which is upstream or downstream and thence, optionally via further plant sections that have not been shut down, recycling said output stream into the plant section said output stream originated from.

2. The process as claimed in claim 1, comprising step (IX).

3. The process as claimed in claim 1, in which the gaseous output stream from the reaction space or, if present, from the separation unit in step I) is used as input stream for the absorption apparatus in VI), wherein the liquid output stream from the absorption apparatus in VI) is conducted via the units for providing phosgene and for mixing into the reaction space and thence, if present, into the separation unit in step I).

4. The process as claimed in claim 1, in which the liquid output stream from the reaction space or, if present, from the separation unit in step I) is used as input stream for the distillation apparatus in step II), wherein the gaseous output stream from the distillation apparatus in step II) is used as input stream for the absorption apparatus in step VI), wherein the liquid output stream from the absorption apparatus in step VI) is conducted via the units for providing phogene and for mixing into the reaction space and thence, if present, into the separation unit in step I).

5. The process as claimed in claim 1, in which the liquid output stream from the reaction space or, if present, from the separation unit in step I) is used as input stream for the distillation apparatus in step II), wherein the liquid output stream from the distillation apparatus in step II) is used as input stream for the distillation apparatus in step III), wherein the gaseous output stream from the distillation apparatus in step III), optionally after condensation in a condenser, is used as input stream for the distillation apparatus in step IV), wherein the liquid output stream from the distillation apparatus in step IV) is conducted via the units for providing solvent, for providing an amine and for mixing into the reaction space and thence, if present, into the separation unit in step I).

6. The process as claimed in claim 1, which additionally comprises a unit for polymer removal in V) wherein the bottoms output stream from the unit for polymer removal, optionally via a storage tank, is used as input stream for the distillation apparatus in step III), wherein the liquid output stream from the distillation apparatus in step III) is recycled into the unit for polymer removal.

7. The process as claimed in claim 1, additionally comprising step (VII) wherein the liquid output stream from the absorption apparatus in step VII), optionally via a storage tank, is recycled back into the absorption apparatus in step VII).

8. The process as claimed in claim 1, in which the amine comprises at least one of methylenediphenyldiamine, polymethylenepolyphenylenepolyamine, a mixture of methylenediphenyldiamine and polymethylenepolyphenylenepolyamine, tolylenediamine, xylylenediamine, hexamethylenediamine, isophoronediamine and naphthyldiamine.

9. A plant for preparation of isocyanates in the liquid phase, comprising the following plant sections:
I) a reaction zone comprising
I.1) a unit for providing an amine in the form of an amine solution in a solvent,
I.2) a unit for providing phosgene in the form of a phosgene solution in a solvent,
I.3) a unit for providing a solvent,
I.4) a mixing unit for mixing the amine solution in the solvent with the phosgene solution in the solvent and optionally further solvent, the mixing unit being configured to be continuously charged with the amine solution in the solvent, the phosgene solution in the solvent, and optionally further solvent, and
I.5) a reaction space arranged downstream of the mixing unit, for conducting a phosgenation reaction, with a separator unit optionally connected downstream, wherein the reaction space and/or the separator unit have outlet conduits for a liquid stream and a gaseous stream;
II) a distillation apparatus configured to separate the liquid stream from I) into a liquid stream and a gaseous stream;
III) a distillation apparatus configured to separate the liquid stream from II) into a gaseous stream and a liquid stream;
IV) a distillation apparatus configured to separate the gaseous stream from III), into a liquid stream and a gaseous stream;
V) a distillation apparatus configured to obtain a liquid isocyanate stream from the liquid stream in III), resulting in a gaseous stream comprising secondary components and optionally solvent, and optionally comprising an upstream unit for polymer removal for removal of polymeric isocyanate fractions;

VI) an absorption apparatus configured to absorb the gaseous streams from I), II) and IV), solvent to obtain a liquid stream and a gaseous stream;

and, optionally

VII) an absorption apparatus configured to absorb the gaseous stream from VI) in water with formation of an offgas stream;

VIII) a workup apparatus for offgas streams, configured to workup offgas streams at least from VII);

and

IX) an apparatus configured to prepare phosgene, and which is connected to the unit for providing phosgene in I);

wherein the plant is configured such that during an interruption of the preparation of isocyanates forced by requirements for maintenance, cleaning or repair in the plant, the entire plant is not stopped, but instead one or more but not all of plant sections I) to IX) are shut down which shut down comprises (A) stopping charging the mixing unit with the amine solution in the solvent and (B) in at least one of the plant sections that have not been shut down,
  (i) recycling an output stream of the at least one plant section which has not been shut down into the respective plant section,
  or
  (ii) conducting an output stream of the at least one plant section which has not been shut down into a plant section which is upstream or downstream and thence, optionally via further plant sections that have not been shut down, recycling said output stream into the plant section said output stream originated from.

10. The plant as claimed in claim 9, comprising process control units for implementing (A).

11. The plant as claimed in claim 9, comprising process control units for implementing (B).

12. The plant as claimed in claim 9, comprising process control units for implementing (A) and (B).

13. A process for operating a plant for preparation of isocyanates in the liquid phase, comprising the following plant sections:

I) a reaction zone comprising
  I.1) a unit for providing an amine, in the form of an amine solution in a solvent,
  I.2) a unit for providing phosgene, in the form of a phosgene solution in a solvent,
  I.3) a unit for providing a solvent,
  I.4) a mixing unit for mixing the amine solution in the solvent with the phosgene solution in the solvent and optionally further solvent, the mixing unit being configured to be continuously charged with the amine solution in the solvent, the phosgene solution in the solvent, and optionally further solvent, and
  I.5) a reaction space arranged downstream of the mixing, for conducting a phosgenation reaction, with a separator unit optionally connected downstream, wherein the reaction space and/or the separator unit have outlet conduits for a liquid stream and a gaseous stream;

II) a distillation apparatus configured to separate the liquid stream from I) into a liquid stream and a gaseous stream;

III) a distillation apparatus configured to separate the liquid stream from II) into a gaseous stream and a liquid stream;

IV) a distillation apparatus configured to separate the gaseous stream from III), into a liquid stream and a gaseous stream;

V) a distillation apparatus configured to obtain a liquid isocyanate stream from the liquid stream from III), resulting in a gaseous stream comprising secondary components and optionally solvent, and which optionally comprises an upstream unit for polymer removal configured to remove polymeric isocyanate fractions;

VI) an absorption apparatus configured to absorb the gaseous streams from I), II) and IV), and in solvent to obtain a liquid stream and a gaseous stream;

VII) optionally, an absorption apparatus configured to absorb the gaseous stream from VI) in water with formation of an offgas stream;

VIII) optionally, a workup apparatus for offgas streams, configured to workup offgas streams at least from VII);

IX) optionally, an apparatus configured to prepare phosgene, and which is connected to the unit for providing phosgene in I);

wherein in the event of a production stoppage the following steps are run:
  (i) stopping the feed of amine into the mixing unit;
  (ii) if present, switching off the apparatus which is configured to prepare phosgene;
  (iii) reducing the phosgene feed into the mixing unit;
  (iv) reducing the solvent feed into the mixing unit;
  (v) running at least one plant section such that the output stream from the respective plant section
    (v)(i) is recycled into the respective plant section,
    or
    (v)(ii) is conducted into a plant section which is upstream or downstream and thence, optionally via further plant sections that have not been shut down, is recycled into the plant section said output stream originated from.

14. The process as claimed in claim 13, which additionally comprises running the following steps after step (v):
  (vi) shutting down at least one plant section;
  (vii) if necessary, opening the at least one plant section that has been shut down in step (vi);
  (viii) conducting a maintenance, cleaning and/or repair measure in the at least one plant section that has been shut down in step (vi);
  (ix) if necessary, closing and optionally, inertizing the at least one plant section that has been shut down in step (vi).

15. The process as claimed in claim 14, which additionally comprises running the following steps after step (ix):
  (x) starting up the at least one plant section shut down in step (vi),
  (xi) if present, starting up the apparatus which is configured to prepare phosgene,
  (xii) starting, the supply of solvent, phosgene and amine in the reaction zone (I).

16. The process as claimed in claim 15, which additionally comprises running the following steps after step (xii):
  (xiii) waiting for feedstocks or auxiliaries and, as soon as these have arrived, (xiv) starting, the supply of solvent, phosgene and amine in the reaction zone (I).

17. The process as claimed in claim 13, in which the amine comprises at least one of methylenediphenyldiamine, polymethylenepolyphenylenepolyamine, a mixture of methylenediphenyldiamine and polymethylenepolyphenylenepolyamine, tolylenediamine, xylylenediamine, hexamethylenediamine, isophoronediamine and naphthyldiamine.

* * * * *